United States Patent
Farrington

(10) Patent No.: US 9,970,969 B1
(45) Date of Patent: May 15, 2018

(54) SYSTEMS, METHODS, AND SOFTWARE FOR DETERMINING SPATIALLY VARIABLE DISTRIBUTIONS OF THE DIELECTRIC PROPERTIES OF A HETEROGENEOUS MATERIAL

(71) Applicant: Transcend Engineering and Technology, LLC, Bethel, VT (US)

(72) Inventor: Stephen P. Farrington, Stockbridge, VT (US)

(73) Assignee: Transcend Engineering and Technology, LLC, Bethel, VT (US)

(*) Notice: Subject to any disclaimer, the term of this patent is extended or adjusted under 35 U.S.C. 154(b) by 17 days.

(21) Appl. No.: 14/813,929

(22) Filed: Jul. 30, 2015

Related U.S. Application Data

(60) Provisional application No. 62/041,739, filed on Aug. 26, 2014.

(51) Int. Cl.
*G01R 27/32* (2006.01)
*G01R 27/06* (2006.01)
(Continued)

(52) U.S. Cl.
CPC .......... *G01R 27/06* (2013.01); *G01N 27/048* (2013.01); *G01N 33/246* (2013.01)

(58) Field of Classification Search
CPC ...... G01N 33/246; G01N 22/00; G01N 22/04; G01N 23/02; G01N 23/08; G01N 9/24;
(Continued)

(56) References Cited

U.S. PATENT DOCUMENTS 4,281,285 A * 7/1981 Bastida .................. G01N 22/04
324/642
4,918,375 A * 4/1990 Malicki ................ G01N 33/246
324/642
(Continued)

FOREIGN PATENT DOCUMENTS

| WO | 1996022522 A1 | 7/1996 |
| WO | 2004109238 A1 | 12/2004 |
| WO | 2011019450 A1 | 2/2011 |

OTHER PUBLICATIONS

"Generalized Pencil-of-Function Method for Extracting Poles of an EM System From Its Transient Response," by Yingbo Hua and Tapan K. Sarkar. IEEE Transactions on Antennas and Propagation, vol. 37, No. 2, pp. 229-234, Feb. 1989.
(Continued)

*Primary Examiner* — Vinh Nguyen
(74) *Attorney, Agent, or Firm* — Downs Rachlin Martin PLLC

(57) ABSTRACT

Systems, methods, and software for measuring the spatially variable relative dielectric permittivity of materials along a linear or otherwise configured sensor element, and more specifically the spatial variability of soil moisture in one dimension as inferred from the dielectric profile of the soil matrix surrounding a linear sensor element. Various methods provided herein combine advances in the processing of time domain reflectometry data with innovations in physical sensing apparatuses. These advancements enable high temporal (and thus spatial) resolution of electrical reflectance continuously along an insulated waveguide that is permanently emplaced in contact with adjacent soils. The spatially resolved reflectance is directly related to impedance changes along the waveguide that are dominated by electrical permittivity contrast due to variations in soil moisture. Various
(Continued)

methods described herein are thus able to monitor soil moisture in profile with high spatial resolution.

12 Claims, 22 Drawing Sheets

(51) Int. Cl.
  *G01N 27/04* (2006.01)
  *G01N 33/24* (2006.01)
(58) Field of Classification Search
  CPC .. G01N 2021/0118; G01N 21/84; G01N 1/44; G01N 27/04; G01N 33/24; G01N 27/048; G01N 19/10; G01N 23/203; G01N 22/02; G01N 2013/003; G01N 23/00; G01N 27/223; G01N 2021/646; G01N 2021/7716; G01N 21/643; G01N 21/8422; G01N 21/952; G01N 2201/0886; G01R 1/06772; G01R 29/0878; G01R 27/04; G01R 31/1245; G01R 31/1272; G01R 31/021; G01R 31/11; G01R 31/12; G01R 31/1263; G01R 31/00; G01R 31/08; G01F 25/0061; G01F 23/266; G01F 23/28; G01F 23/2962; G01F 1/7048; G06F 17/16; G06F 17/5009; H01P 3/16; H01P 3/10; H01P 1/00; H01P 5/00; H01P 5/02; H01P 5/08; H01P 5/087; H01P 5/103
  See application file for complete search history.

(56) References Cited

U.S. PATENT DOCUMENTS

| | | | |
|---|---|---|---|
| 5,176,207 A | 1/1993 | Keller | |
| 5,459,403 A | 10/1995 | Kohler et al. | |
| 5,483,169 A | 1/1996 | Despain et al. | |
| 5,570,030 A | 10/1996 | Wightman | |
| 5,621,669 A | 4/1997 | Bjornsson | |
| 5,631,562 A | 5/1997 | Cram et al. | |
| 5,818,241 A | 10/1998 | Kelly | |
| 6,060,889 A | 5/2000 | Hocker | |
| 6,079,433 A | 6/2000 | Saarem | |
| 6,281,688 B1 | 8/2001 | Yankielun | |
| 6,281,801 B1* | 8/2001 | Cherry | G01N 33/246 324/643 |
| 6,283,209 B1 | 9/2001 | Keller | |
| 6,298,920 B1 | 10/2001 | Keller | |
| 6,313,645 B1 | 11/2001 | Brandelik et al. | |
| 6,441,622 B1 | 8/2002 | Wrzesinski et al. | |
| 6,507,200 B2 | 1/2003 | Brandelik et al. | |
| 6,696,974 B1 | 2/2004 | Mathis | |
| 6,910,374 B2 | 6/2005 | Keller | |
| 6,956,381 B2 | 10/2005 | Dahan | |
| 6,989,676 B2 | 1/2006 | Nagy | |
| 7,040,145 B2 | 5/2006 | Drnevich et al. | |
| 7,126,352 B2 | 10/2006 | Bernhard | |
| 7,135,871 B1 | 11/2006 | Pelletier | |
| 7,176,697 B1 | 2/2007 | Dahan | |
| 7,228,900 B2 | 6/2007 | Schultz et al. | |
| 7,281,422 B2 | 10/2007 | Keller | |
| 7,562,832 B1 | 7/2009 | Anderson | |
| 7,777,496 B2 | 8/2010 | Evans et al. | |
| 7,791,355 B1 | 9/2010 | Esher et al. | |
| 8,176,977 B2 | 5/2012 | Keller | |
| 8,350,580 B2* | 1/2013 | Woodhead | G01R 27/04 324/639 |
| 8,381,582 B2 | 2/2013 | Dahan | |
| 8,494,775 B2 | 7/2013 | Parsche | |
| 8,525,527 B2 | 9/2013 | Skaling | |
| 8,901,939 B2 | 12/2014 | Skaling | |
| 8,912,805 B2 | 12/2014 | Schroeder | |
| 2003/0024155 A1 | 2/2003 | Kuroda et al. | |
| 2003/0042916 A1 | 3/2003 | Anderson | |
| 2003/0071637 A1 | 4/2003 | Dahan | |
| 2005/0212532 A1 | 9/2005 | Bernhard | |
| 2007/0273394 A1 | 11/2007 | Philip et al. | |
| 2009/0212789 A1 | 8/2009 | Lin et al. | |
| 2009/0293354 A1 | 12/2009 | Goldberg et al. | |
| 2010/0013497 A1* | 1/2010 | Evans | G01N 21/84 324/642 |
| 2011/0006785 A1* | 1/2011 | Gradinarsky | G01N 22/00 324/640 |
| 2015/0022220 A1 | 1/2015 | Tixier et al. | |
| 2015/0028890 A1 | 1/2015 | Troxler | |

OTHER PUBLICATIONS

"Feasibility of Sequential and Coupled Inversion of Time Domain Reflectometry Data to Infer Soil Hydraulic Parameters Under Falling Head Infiltration," by C.M. Mboh, J.A. Huisman and H. Vereecken. SSSAJ: vol. 75: No. 3, pp. 775-786, May 2011.

"Comprehensive Wave Propagation Model to Improve TDR Interpretations for Geotechnical Applications," by Chih-Ping Lin and Shr-Hong Tang. Geotechnical Testing Journal, vol. 30, No. 2, Paper ID GTJ100012, May 2015.

"Analysis of Nonuniform and Dispersive Time Domain Reflectometry Measurement Systems With Application to the Dielectric Spectroscopy of Soils," by C.-P. Lin. Water Resources Research, vol. 39, No. 1, 1012 (2003).

"High-Resolution Moisture Profiles From Full-Waveform Probabilistic Inversion of TDR Signals," by Eric Laloy, Johan Alexander Huisman, and Diederik Jacques. Journal of Hydrology 519 (2014) pp. 2121-2135.

"A Review of Advances in Dielectric and Electrical Conductivity Measurement in Soils Using Time Domain Reflectometry," by D.A. Robinson, S.B. Jones, J.M. Wraith, D. Or and S.P. Friedman. Vadose Zone Journal 2:444-475 (2003).

"Spatially Resolved Water Content Profiles From Inverted Time Domain Reflectometry Signals," by B. Oswald. Water Resources Research, vol. 39, No. 12, 1357 (2003).

"A Time Domain Reflectometry Borehole Packer for Use in Rock," by S.W. Truss, L.J. West, P. Winship, M. Nakhkash and Y. Huang. The University of Liverpool, School of Earth Sciences, University of Leeds (2001).

"Measurement and Modeling of the TDR Signal Propagation Through Layered Dielectric Media," by M.G. Schaap, D.A. Robinson, S.P. Friedman, and A. Lazar. Soil Science Society of America Journal, Jul./Aug. 2003, vol. 67, No. 4; Sciences Module pp. 1113-1121.

"Laboratory Measurements of Electromagnetic Wave Velocity in Layered Sands," by Christina Y. Chan and Rosemary J. Knight. Water Resources Research, vol. 37, No. 4, pp. 1099-1105, Apr. 2001.

"The Time-Domain Reflectometry Method for Measuring Soil Water Content and Salinity," by F.N. Dalton and M. Th. Van Genuchten. Elsevier Science Publishers B.V. Amsterdam, Geoderma, 38 (1986) pp. 237-250.

"Soil-Crop Dynamic Depth Response Determined from TDR of a Corn Silage Field Compared to EMI Measurements," by Bryan L. Woodbury, Roger A. Eigenberg, John A. Nienaber and Mindy J. Spiehs. JEEG, Sep. 2010, vol. 15, Issue 3, pp. 185-196.

"Spatial Time Domain Reflectometry (Spatial TDR) for Moisture Monitoring in Geological Repositories—Technology, Feasibility, and Limitations," by Norman Wagner, Klaus Kupfer, Eberhard Trinks, Michael Kuhne, Frank Bonitz and Bernd Muller. Institute of Material Research and Testing (MFPA) at the Bauhaus-University Weimar, Germany (Mar. 2013) (paper version).

"Spatial Time Domain Reflectometry (Spatial TDR) for Moisture Monitoring in Geological Repositories—Technology, Feasibility, and Limitations," by Norman Wagner, Klaus Kupfer, Eberhard Trinks, Michael Kuhne, Frank Bonitz and Bernd Muller. Institute of Material Research and Testing (MFPA) at the Bauhaus-University Weimar, Germany (Mar. 2013) (slide version).

(56) References Cited

OTHER PUBLICATIONS

"Continuous Measurements of Liquid Water Content and Density in Snow Using TDR," by Peter Waldner, Chrisof Huebner, Martin Schneebeli, Alexander Brandelik, and Frank Rau. TDR 2001—Proceedings of the Second International Symposium and Workshop on Time Domain Reflectometry for Innovative Geotechnical Applications, Charles H. Dowding (Ed.), Sep. 5-7, 2001, Infrastructure and Technology Institute at Northwestern University, Evanston, IL, USA. http://www.iti.northwestern.edu/tdr/tdr2001/proceedings/.

"A Fast TDR-inversion technique for the reconstruction of spatial soil moisture content," by S. Schlaeger. Hydrology and Earth System Sciences, 9, 481-492, 2005.

"Spatial-TDR Moisture Measurement in a Large Scale Levee Model Made of Loamy Soil Material," by Holger Worsching, Rolf Becker, Stefan Schlaeger, Andreas Bieberstein, and Peter Kudella. Proc. TDR 2006, Purdue University, West Lafayette, USA, Sep. 2006, Paper ID 33, 15 p., https://engineering.purdue.edu/TDR/Papers.

"Measurement of Soil Bulk Electrical Conductivity Using Partially Coated TDR Probes," by D. Moret-Fernandez, F. Lera, J.L. Arrue, and M. V. Lopez. Vadose Zone Journal, vol. 8, No. 3, pp. 594-600 (Aug. 2009).

"Spatial time domain reflectometry and its application for the measurement of water content distributions along flat ribbon cables in a full-scale levee model," by Alexander Scheuermann, Christof Huebner, Stefan Schlaeger, Norman Wagner, Rolf Becker, and Andreas Bieberstein. Water Resources Research, vol. 45, W00D24 (2009).

* cited by examiner

SYSTEMS, METHODS, AND SOFTWARE FOR DETERMINING SPATIALLY VARIABLE DISTRIBUTIONS OF THE DIELECTRIC PROPERTIES OF A HETEROGENEOUS MATERIAL

RELATED APPLICATION DATA

This application claims the benefit of priority of U.S. Provisional Patent Application Ser. No. 62/041,739, filed on Aug. 26, 2014, and titled "Systems and Methods for Determining Spatially Variable Distributions of the Dielectric Properties of a Heterogeneous Material," which is incorporated by reference herein in its entirety.

STATEMENT REGARDING FEDERALLY SPONSORED RESEARCH OR DEVELOPMENT

This invention was made with U.S. government support under SBIR Grant DE-SC0009646 awarded by the Department of Energy. The government has certain rights in the invention.

FIELD OF THE INVENTION

The present invention generally relates to the field of measuring and testing. In particular, the present invention is directed to systems, methods, and software for determining spatially variable distributions of the dielectric properties of a heterogeneous material.

BACKGROUND

Various attempts to produce meaningful analytics of electrical properties of materials have resulted in development of systems and methods that are usable in particular instances for particular purposes but that are not suitable or optimized for, e.g., ascertaining a spatial profile of electrical or dielectric properties of the materials. Due to various shortcomings of the prior art, new technologies need to be developed to increase the quality of analytical methodologies available to geologists, security professionals, and government officials, among others.

SUMMARY OF THE DISCLOSURE

Aspects of the present disclosure provide a method and system for measuring the spatially variable relative dielectric permittivity of materials along a linear or otherwise configured sensor element, and more specifically the spatial variability of soil moisture in one dimension as inferred from the dielectric properties of the soil matrix surrounding a linear sensor element.

In one implementation, method of determining spatially variable distributions of dielectric properties of a material having at least one dielectric constant using an insulated parallel waveguide disposed proximal to the material in which the spatial profile of moisture or related electrical properties is to be determined is provided. Such a method may include: using the insulated parallel waveguide to perform a time domain reflectometry (TDR) measurement to acquire a temporal profile of apparent reflectance of the waveguide; converting the temporal profile of apparent reflectance of the waveguide to a spatial profile of a quantity that is indicative of one or more electrical properties of a portion of the material adjacent to the waveguide; and converting the spatial profile to a second spatial profile of moisture content of the material by correlating impedance characteristics associated with the waveguide to the at least one dielectric constant of the portion of the material adjacent to the waveguide as a function of a predetermined relationship determined via numerical modeling.

In another implementation, a method of determining spatially variable distributions of the dielectric properties of a material having at least one dielectric constant is provided. Such a method may include: disposing an insulated parallel waveguide proximal to the material in which the spatial profile of moisture or related electrical properties is to be determined; using the insulated parallel waveguide to perform a TDR measurement to acquire a first temporal profile of apparent reflectance of the waveguide; converting the first temporal profile of apparent reflectance of the waveguide to a second temporal profile of a quantity that is indicative of one or more electrical properties of a portion of the material adjacent to the waveguide; and converting the second temporal profile to a spatial profile of moisture content of the material by correlating impedance characteristics associated with the waveguide to the at least one dielectric constant of the portion of the material adjacent to the waveguide as a function of a predetermined relationship determined via numerical modeling.

In still another implementation, a machine-readable storage medium containing machine-executable instructions for performing a method of determining spatially variable distributions of the dielectric properties of a material having at least one dielectric constant using an insulated parallel waveguide disposed proximal to the material in which the spatial profile of moisture or related electrical properties is to be determined is provided. Such a machine-readable storage medium may include: a first set of machine-executable instructions for using the insulated parallel waveguide to perform a TDR measurement to acquire a temporal profile of apparent reflectance of the waveguide; a second set of machine-executable instructions for converting the temporal profile of apparent reflectance of the waveguide to a spatial profile of a quantity that is indicative of one or more electrical properties of a portion of the material adjacent to the waveguide; and a third set of machine-executable instructions for converting the spatial profile to a second spatial profile of moisture content of the material by correlating impedance characteristics associated with the waveguide to the at least one dielectric constant of the portion of the material adjacent to the waveguide as a function of a predetermined relationship determined via numerical modeling.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

Aspects of the present invention include systems, methods, and software for determining spatially variable distributions of the dielectric properties of a heterogeneous material. In some embodiments, an insulated, flexible waveguide disposed in or proximal to a material can be used to analyze electrical properties of the material(s) by applying controlled electrical excitations to the waveguide and monitoring reflections or other consequences of such excitations. By utilizing aspects of the present disclosure, a spatial profile of electrical or dielectric properties of materials can be produced as a function of reflections or other consequences of such excitations.

Figure 1:
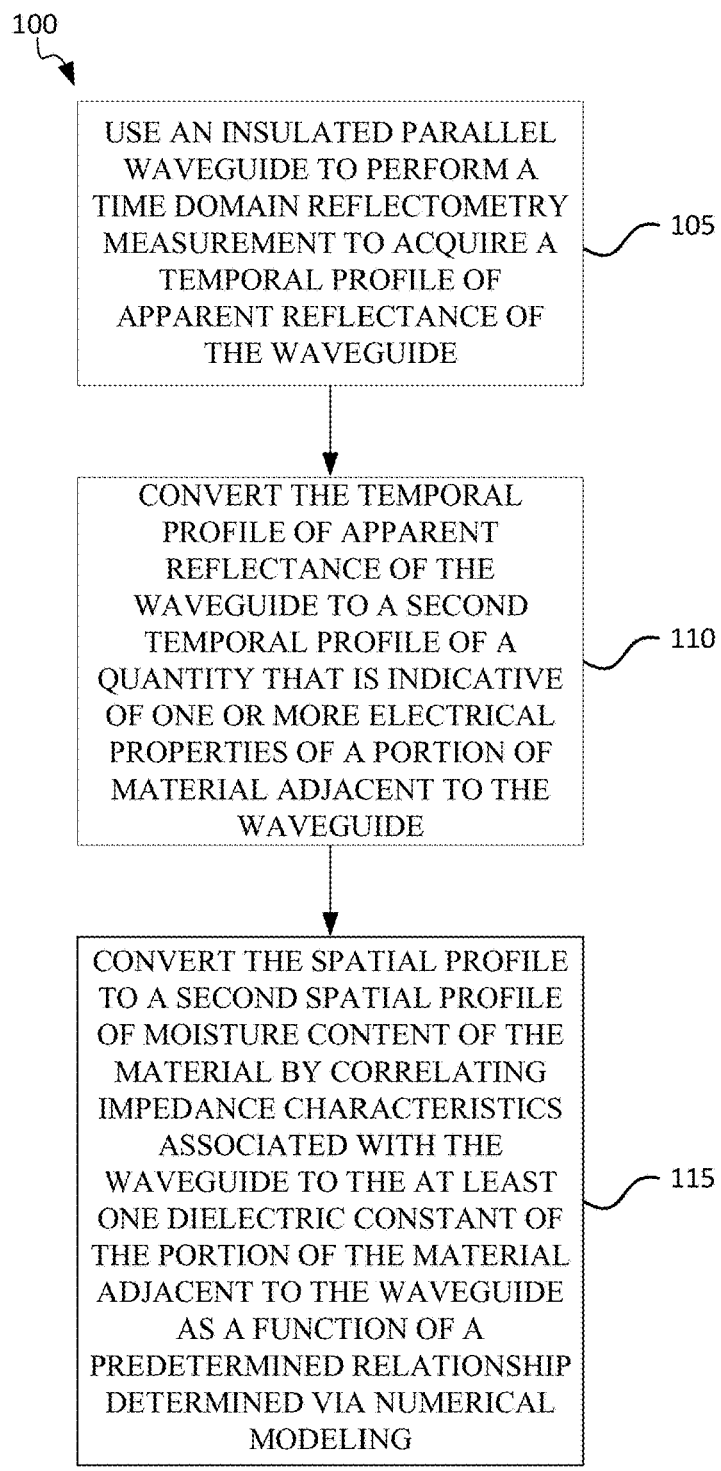
FIG. 1 is a flow diagram illustrating a method of determining spatially variable distributions of dielectric properties of a material having at least one dielectric constant using an insulated parallel waveguide disposed proximal to the material in which the spatial profile of moisture or related electrical properties is to be determined.

Referring now to the drawings, FIG. 1 illustrates an exemplary method 100 of determining spatially variable distributions of dielectric properties of a material having at least one dielectric constant using an insulated parallel waveguide disposed proximal to the material in which the spatial profile of moisture or related electrical properties is to be determined. In this example, method 100 includes: using the insulated parallel waveguide to perform a time domain reflectometry (TDR) measurement to acquire a temporal profile of apparent reflectance of the waveguide (step 105); converting the temporal profile of apparent reflectance of the waveguide to a spatial profile of a quantity that is indicative of one or more electrical properties of a portion of the material adjacent to the waveguide (step 110); and converting the spatial profile to a second spatial profile of moisture content of the material by correlating impedance characteristics associated with the waveguide to the at least one dielectric constant of the portion of the material adjacent to the waveguide as a function of a predetermined relationship determined via numerical modeling (step 115). Details of method 100 and associated steps are described further herein.

Figure 2:
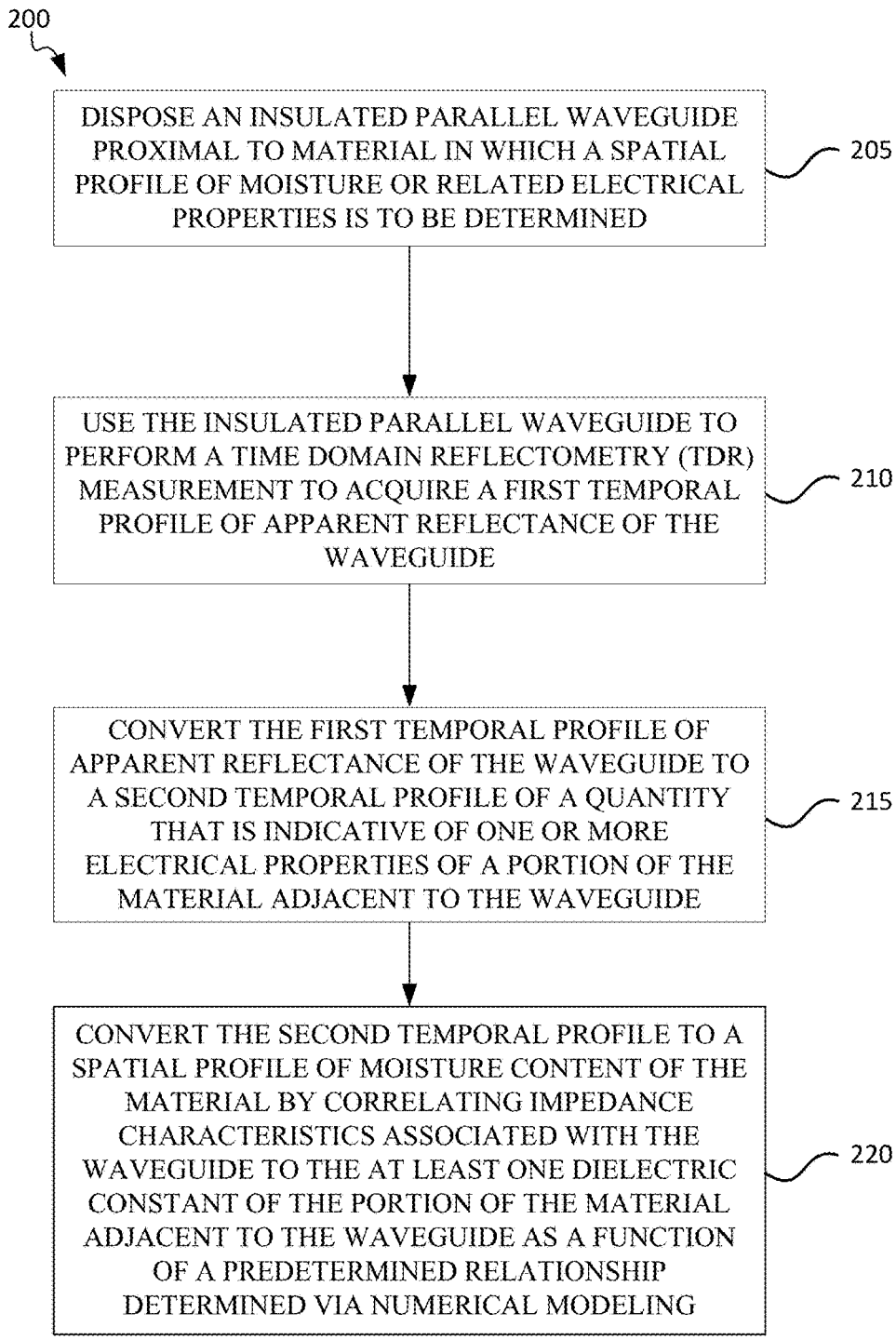
FIG. 2 is a flow diagram illustrating a method of determining spatially variable distributions of the dielectric properties of a material having at least one dielectric constant.

FIG. 2 illustrates an exemplary method 200 of determining spatially variable distributions of the dielectric properties of a material having at least one dielectric constant. In this example method 200 includes: disposing an insulated parallel waveguide proximal to the material in which spatial profile of moisture or related electrical properties is to be determined (step 205); using the insulated parallel waveguide to perform a time domain reflectometry measurement to acquire a first temporal profile of apparent reflectance of the waveguide (step 210); converting the first temporal profile of apparent reflectance of the waveguide to a second temporal profile of a quantity that is indicative of one or more electrical properties of a portion of the material adjacent to the waveguide (step 215); and converting the second temporal profile to a spatial profile of moisture content of the material by correlating impedance characteristics associated with the waveguide to the at least one dielectric constant of the portion of the material adjacent to the waveguide as a function of a predetermined relationship determined via numerical modeling (step 220). Details of method 200 and associated steps are described further herein.

Figure 21:
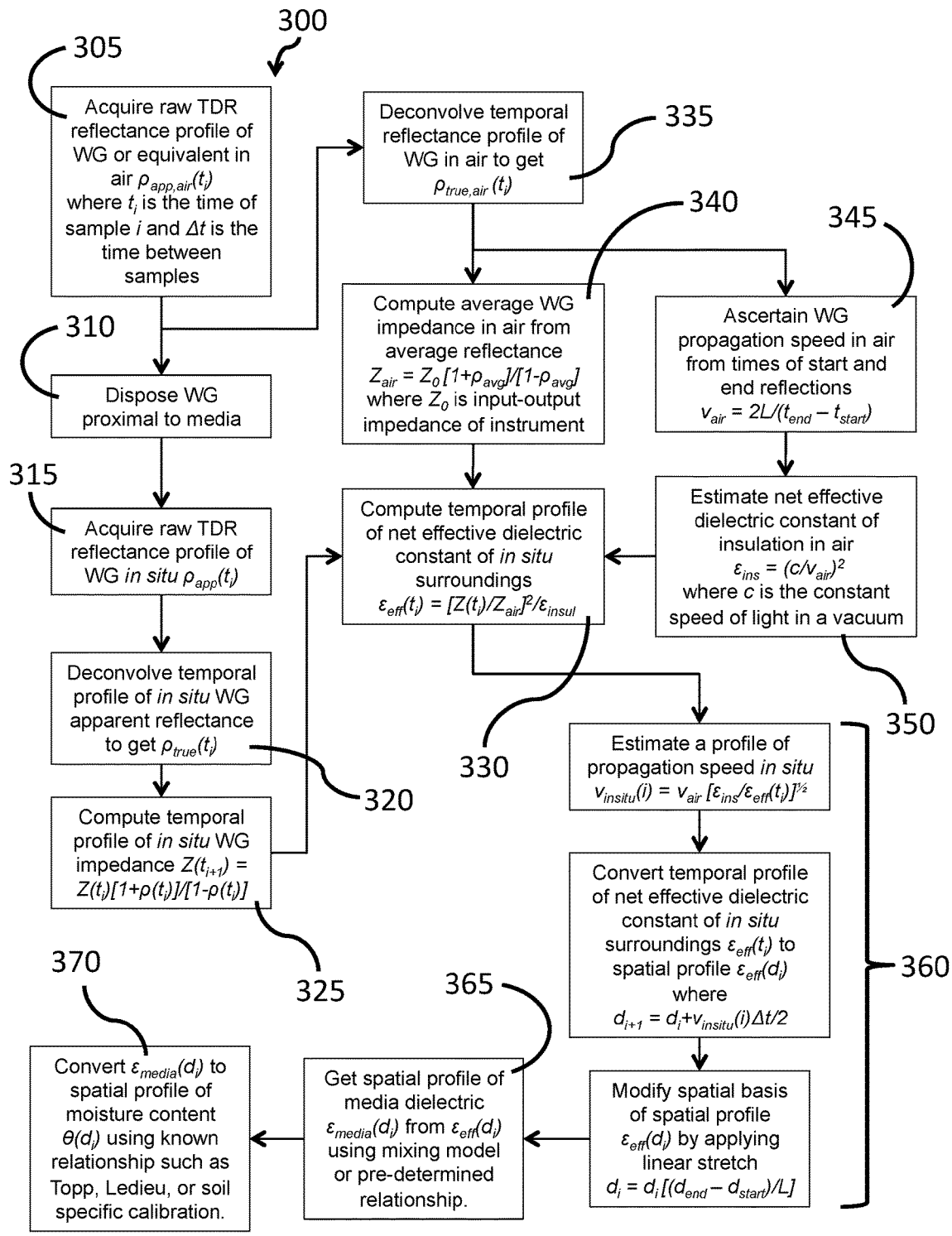
FIG. 21 is a flow diagram illustrating a method of determining spatially variable distributions of dielectric properties of a material having at least one dielectric constant.

FIG. 21 illustrates an exemplary method 300 of determining spatially variable distributions of the dielectric properties of a material having at least one dielectric constant. In this example, method 300 includes: acquiring a TDR reflectance profile of an insulated parallel waveguide disposed in air (step 305); disposing the insulated parallel waveguide proximal to the material in which the spatial profile of moisture or related electrical properties is to be determined (step 310); using the insulated parallel waveguide to perform a time domain reflectometry measurement to acquire a first temporal profile of apparent reflectance of the waveguide (step 315); deconvolving the first temporal profile of apparent reflectance of the waveguide to produce a second temporal profile of the true reflectance of the waveguide (step 320); converting the second temporal profile of true reflectance of the waveguide to a third temporal profile of the characteristic impedance of the waveguide (step 325); converting the third temporal profile of the characteristic impedance of the waveguide to a fourth temporal profile of at least one effective dielectric constant of the materials surrounding the waveguide (step 330) using electrical properties of the waveguide in air determined from measurements of the waveguide or an equivalent waveguide disposed in air (steps 335, 340, 345, and 350); converting the fourth temporal profile of the at least one dielectric constant of the materials surrounding the waveguide to a first spatial profile of the at least one dielectric constant of the materials surrounding the waveguide (step 360); converting the first spatial profile of the at least one dielectric constant of the materials surrounding the waveguide to a second spatial profile of at least one dielectric constant of the soil media adjacent to one side of the waveguide (step 365); and converting the second spatial profile of the at least one dielectric constant of the soil media adjacent to one side of the waveguide to a third spatial profile of the moisture content of the media adjacent to the waveguide, using a predetermined relationship such as the Topp equation, the Ledieu equation, or a soil specific calibration relating soil moisture content to soil dielectric constant (step 370). Details of method 300 and associated steps are described further herein.

Soil is a three-component mixture of materials in solid, gaseous, and liquid phases. The solid phase consists of soil particles which pack to form a structure or matrix having interconnected pore spaces. These pores contain liquid and/or gas (typically air) into and through which water or other liquid may flow or remain stationary. The dielectric constant of air is 1 by definition. The dielectric constant of dry soils is generally in the range of 2.5 to 4.0, and the dielectric constant of water is around 78 at room temperature. The high contrast between the dielectric constant of water and that of the other two materials in a soil matrix allows the moisture content of soils to be inferred from measurement of the dielectric constant of the mixed media.

Figure 6:
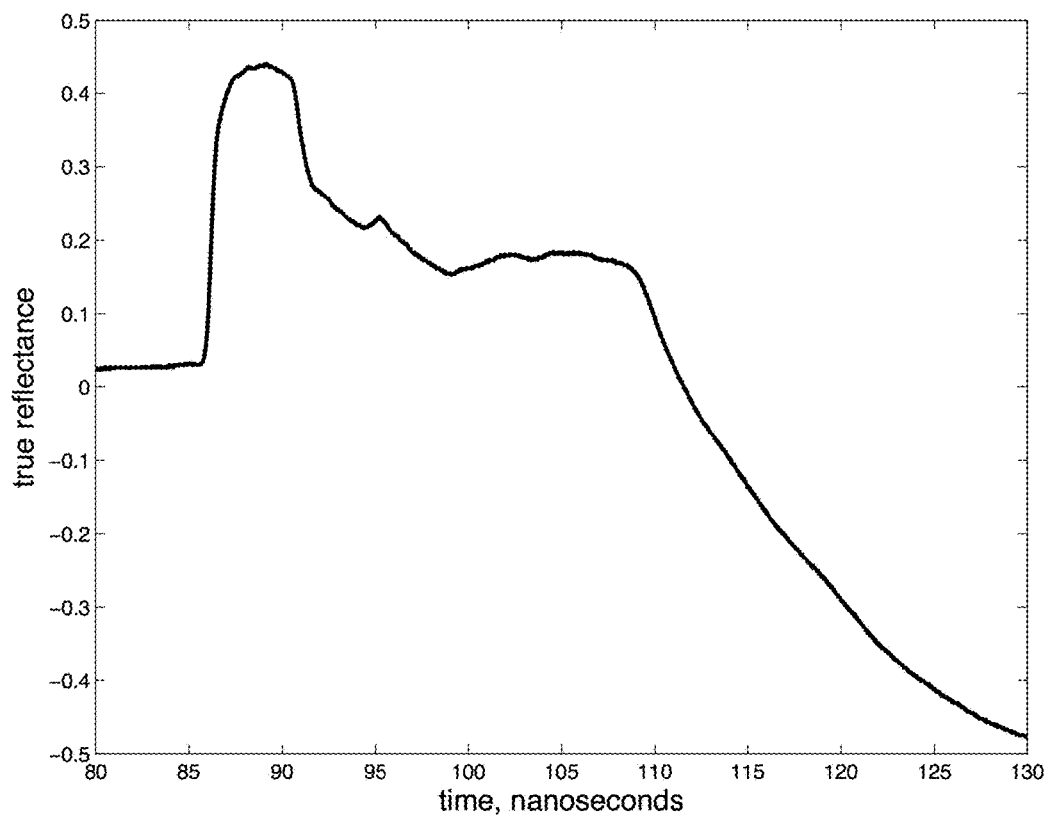
FIG. 6 is a plot showing a temporal profile of true reflectance acquired by performing deconvolution to remove multi-reflection effects from a profile of apparent reflectance.
Figure 7:
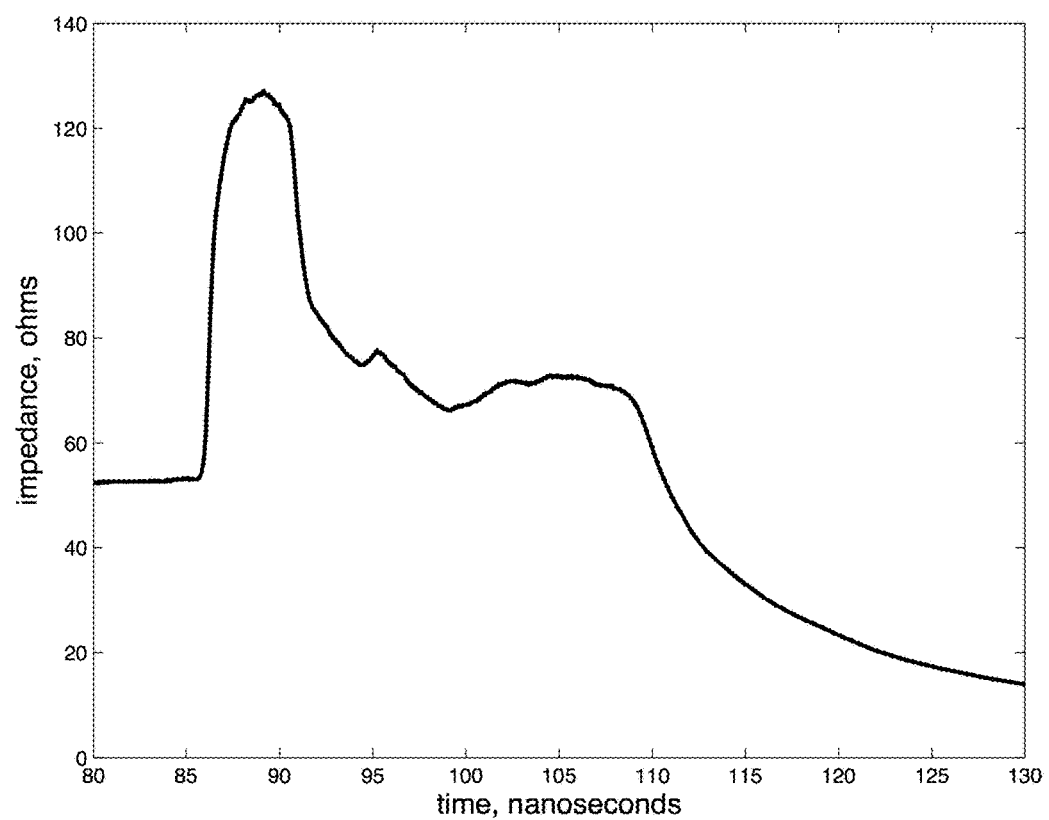
FIG. 7 is a plot showing a temporal profile of waveguide impedance obtained from a temporal profile of true reflectance.
Figure 18:
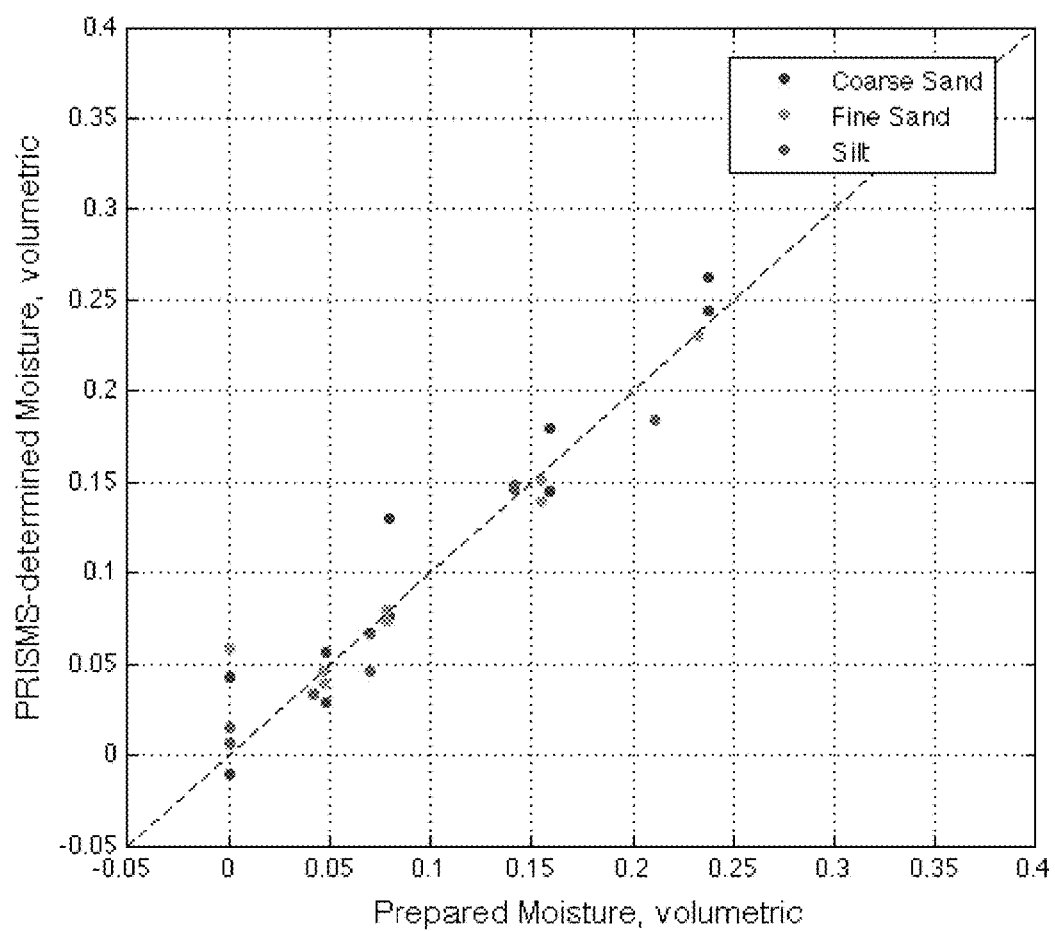
FIG. 18 is a plot showing strong correlation between determinations of soil moisture made using the present method and the gravimetrically prepared water content.
Figure 19:
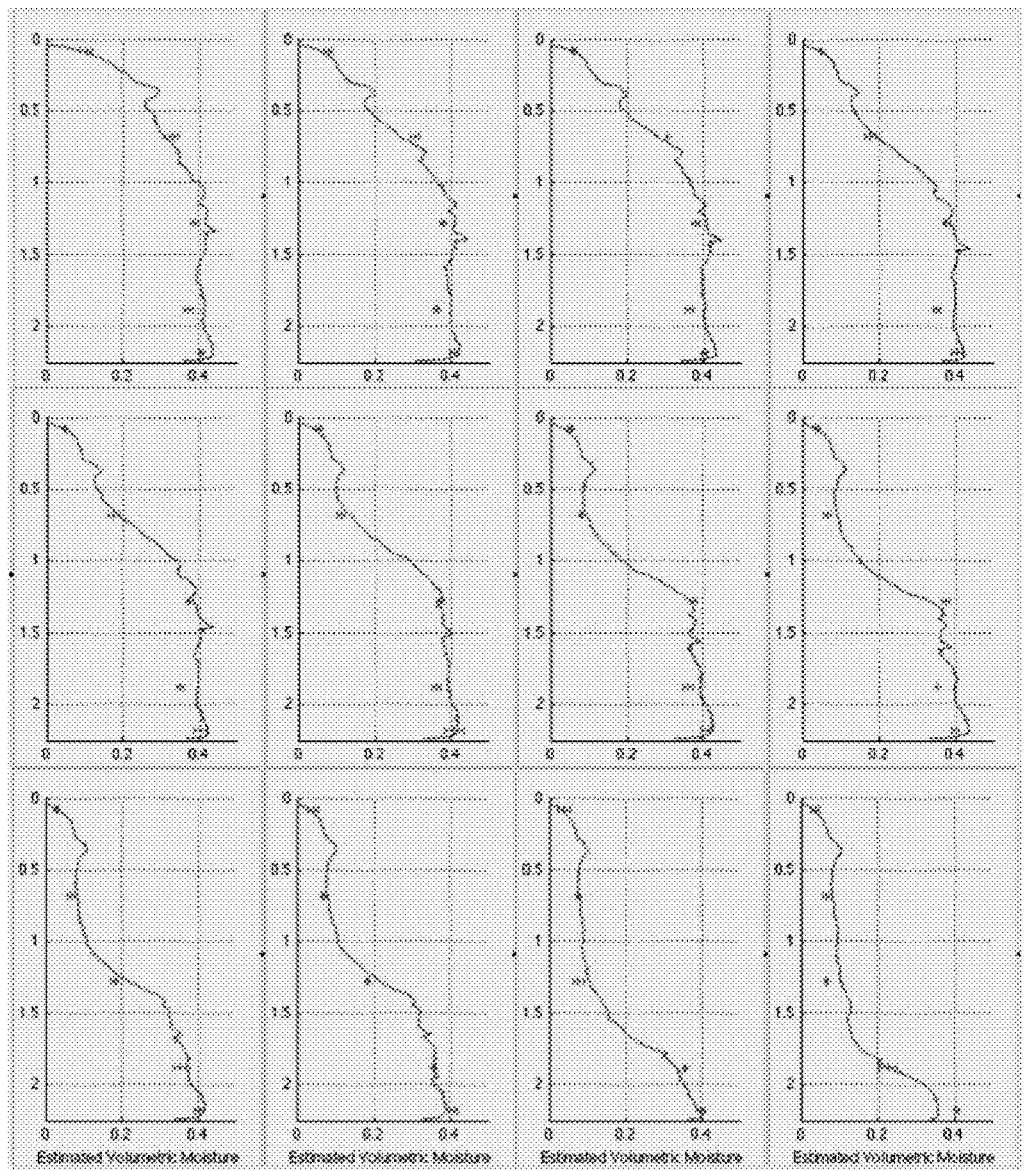
FIG. 19 is a series of plots from a soil column experiment showing comparison of moisture profiles determined using the presently disclosed method to discrete (distance averaged) measurements made using conventional TDR probes.
Figure 20:
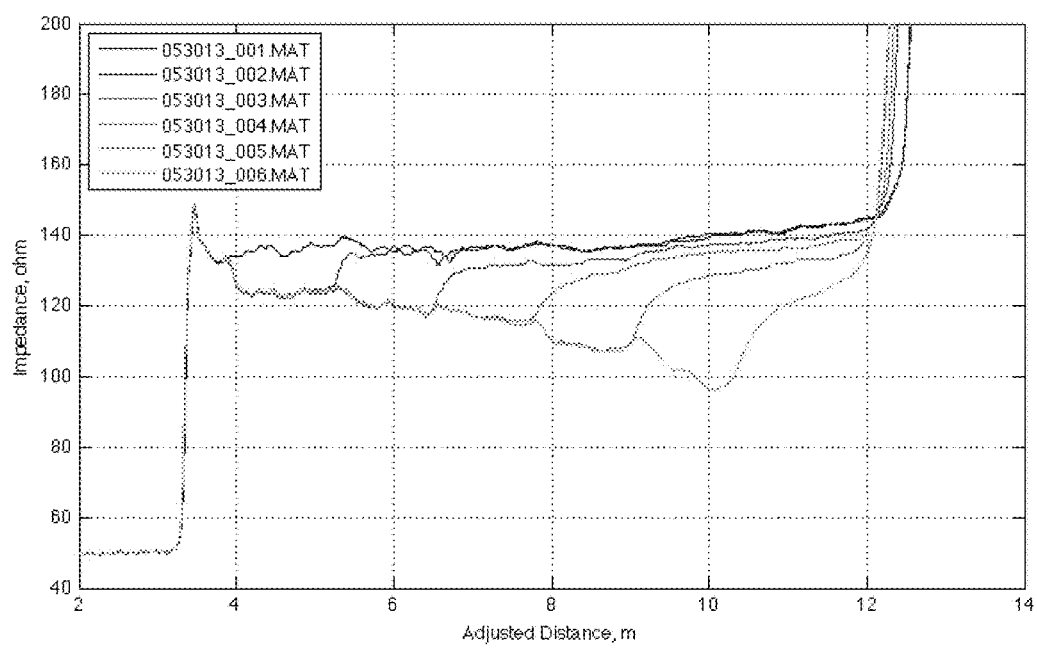
FIG. 20 is a plot showing spatial profiles of transmission line impedance obtained from converting temporal profiles of true reflectance after performing deconvolution to obtain true reflectance from apparent reflectance.

Various methods provided herein combine advances in the processing of TDR data with innovations in the physical sensing apparatus. These advancements enable high temporal (and thus spatial) resolution of electrical reflectance continuously along an insulated waveguide that is permanently emplaced in contact with adjacent soils. The spatially resolved reflectance is directly related to impedance changes along the waveguide that are dominated by electrical permittivity contrast due to variations in soil moisture. Various methods described herein are thus able to monitor soil moisture in profile with high spatial resolution. FIG. 18, which shows correlation between determinations of soil moisture made using aspects of the present disclosure and conventional TDR measurements performed on soil of a gravimetrically prepared water content, also illustrates the difference between the spatially continuous measurement aspect of the present disclosure in comparison to the spatially discrete aspect of conventional TDR soil moisture measurements. The vertical axis of FIG. 6 is labeled "volumetric" soil moisture content, which is computed from the gravimetric content knowing the soil porosity.

Various methods described herein use an electrically insulated transmission line, also known as a waveguide. With few exceptions, soil moisture sensors that use the principle of time domain reflectometry have typically comprised transmission lines that are in continuous electrical contact (e.g., galvanically coupled) with the medium being tested. The medium itself is conductive to varying degrees in a spatially heterogeneous manner, so that both the magnitude and time of arrival the energy returned to the time domain reflectometer by reflection from impedance contrasts along the transmission line, as described by conventional transmission line theory, are affected by both the electrical conductivity and the dielectric constant of the medium through which the transmission line passes.

Figure 16:
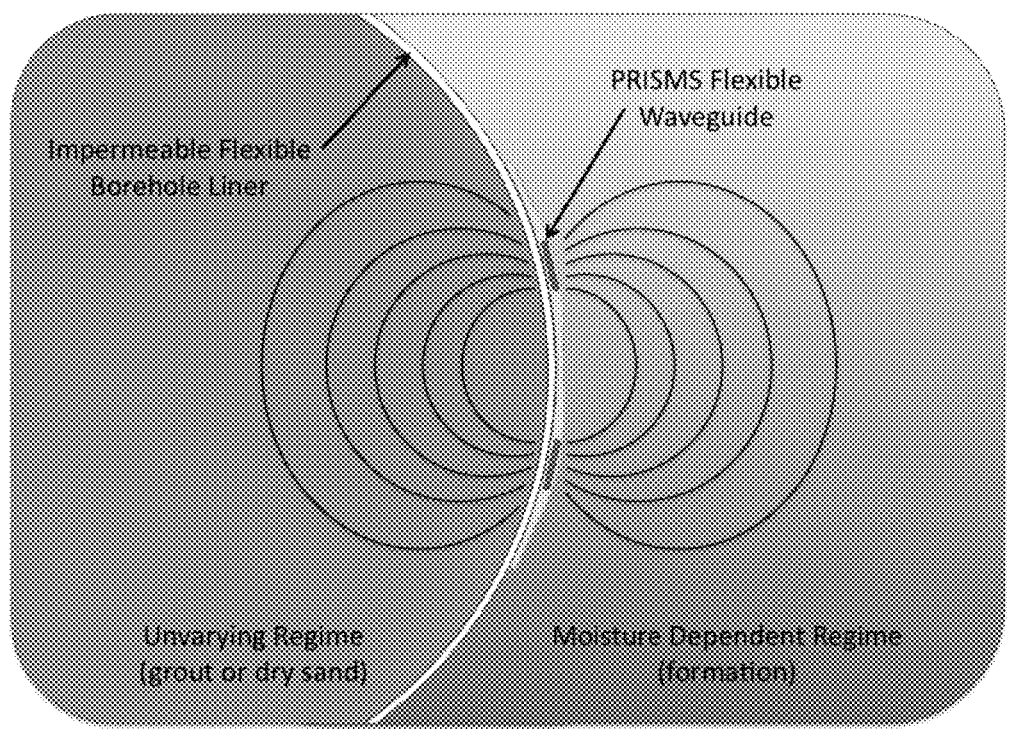
FIG. 16 is a transverse view of a cross-section of a waveguide with auxiliary structures used to dispose it in proximity to the material under test, also showing the penetration into the surrounding media of the electric field generated by the incident TDR pulse.
Figure 17:
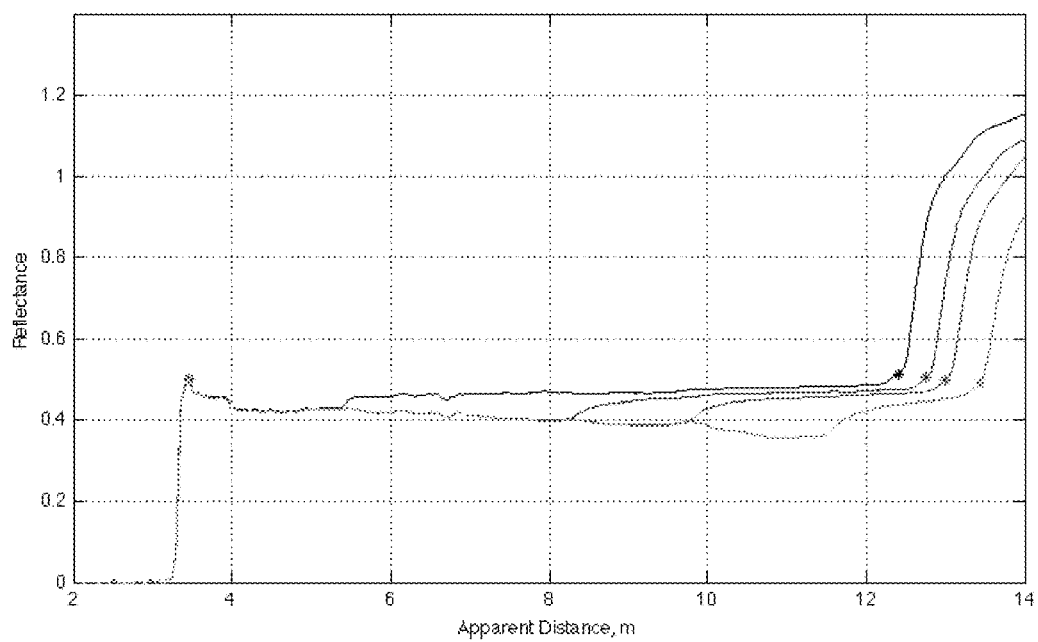
FIG. 17 is a graph of unprocessed apparent reflectance profiles from coarse sand arranged in four different spatial sequences of soil moisture content showing the effect of dielectric dependent characteristic impedance changes on incident pulse travel velocity as evident in the variable shift of the final reflection from the distal end of a waveguide.

An aspect of the present disclosure is the physical design of the waveguide in which electrical insulation coating the conductors inhibits loss of energy due to the electrical conductivity of the material under test and the dimensions and spatial relationships of the conductors and insulation in the planar transmission line is effective for causing the electric field formed by an incident voltage pulse traveling on the line to extend substantially into the media adjacent to the line, thus ensuring sensitivity of the measurement to the electrical properties of the media under test. FIG. 16 shows a representation of electric field lines extending into the media under test. The lines shown are oriented in the direction of current. Lines showing equipotential voltage would be oriented perpendicular to the current lines.

Electrically insulating the transmission line from adjacent materials significantly reduces the transverse conductance of the transmission line such that in many soil conditions the effects of transverse conductance on observed transmission line behavior is negligible. In low conductivity soils, this reduction in the effect of conductance enables the dielectric profile of the media adjacent to the transmission line to be recovered directly from the impedance profile of a transmission line of uniform cross sectional geometry obtained from the reflectance profile.

For transmission lines in significantly conductive media, the apparent reflectance profile is also affected by losses in the media, so recovery of impedance profiles, velocity profiles, and related material dielectric profiles from measured reflectance profiles in lossy media may introduce artifacts that distort the profiles. Knowing the length of the transmission line and determining, a priori, its characteristic impedance and propagation velocity enables correction of the effects of lossy media.

Another aspect of the present disclosure is the data process that is used to interpret the TDR signal acquired from the linear sensor element and to spatially register the inherently time-domain information. The data process includes an algorithm that deconvolves the time domain signal to remove multi-reflection effects also referred to as reverberation. Additional algorithms enable electrical parameters measured in the time domain to be converted to the spatial domain by accounting for the spatially variable propagation speed of an incident electrical pulse launched into the waveguide and its measured reflections. This aspect of the process enables spatial resolution of variations in the media dielectric constant and, thus, soil moisture content in profile. Still more data processes estimate the spatial distribution of variability in media dielectric constant and soil moisture content in one dimension co-aligned with the sensor element.

When disposing of the waveguide in proximity to the material under test requires the introduction of additional structural support elements to form a waveguide assembly, then another significant aspect of the present disclosure is the way in which the influence of the dielectric properties of the additional support materials is accounted for in the interpretation of the signals measured to recover the dielectric profile of the media under test from the gross effective dielectric profile of the combination of media and the waveguide support materials/additional introduced structures.

A method performed in accordance with the present disclosure may comprise: (1) disposing an insulated parallel waveguide proximal to the material in which the spatial profile of moisture or related electrical properties is to be determined; (2) performing a TDR measurement of the parallel waveguide of Step 1 to acquire the temporal profile of apparent reflectance; (3) converting the temporal profile of reflectance obtained in Step 2 to a temporal or spatial profile of a quantity that is indicative of one or more electrical properties of materials adjacent to the transmission line; and (4) converting the temporal or spatial profile a quantity that is indicative of the electrical properties of materials adjacent to the transmission line obtained in Step 3 to a spatial profile of moisture content. Detailed methods of performing each step are described below.

Step 1

Figure 3:
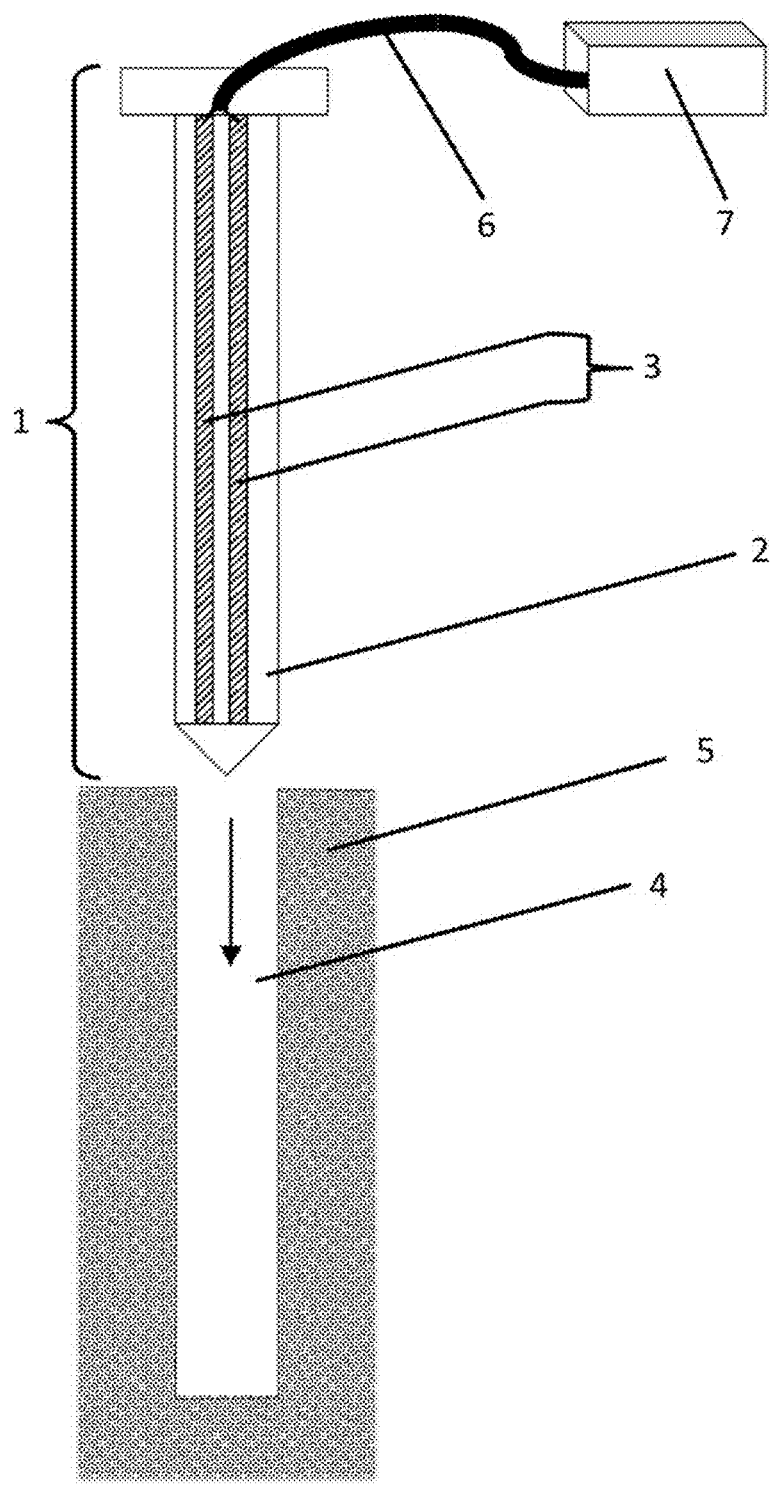
FIG. 3 is a side view of a probe comprising a substantially cylindrical body with a waveguide embedded in the wall thereof being inserted into a cavity in soil.

Many methods are suitable for disposing an insulated parallel waveguide proximal to the material in which the spatial profile of moisture or related electrical properties is to be determined performing Step 1. A particular method applicable to measuring soil moisture in horizontal profile is to directly bury the waveguide in an approximately horizontal trench in the soil. A particular method suitable for measuring vertical distributions of soil moisture over depths of, for instance, one to two meters, as may be required for agricultural applications, is to form a vertically oriented or other oriented hole in the soil using a rotary auger or other means of forming a cavity and to insert into the hole a probe comprising a plastic, fiberglass, or other non-metallic tube, rod, or other rigid or semi-rigid member bearing the waveguide adhered to the outside of the member or incorporated into the wall thereof. The probe may also be pushed or driven into the ground without first creating a hole. FIG. 3 is a side view of a probe 1 comprising a substantially cylindrical body 2 with a waveguide 3 embedded in the wall thereof, being inserted into a hole 4 in the soil 5. A coaxial cable 6 may connect waveguide 3 to a TDR instrument or other measurement instrumentation 7. Waveguide 3 may also be connected directly to measurement instrumentation 7 (e.g., TDR instrument or reflectometer) or to electronic circuitry that performs the equivalent functions of a reflectometer. Another particular method applicable to installation of waveguides in deeper boreholes is disclosed in U.S. Provisional Patent Application Ser. No. 62/030,977 filed on Jul. 30, 2014, and titled "Systems, Methods, and Apparatuses for Measuring Electrical Properties of a Material," the subject matter of which was invented by the present inventor and the disclosure of which is hereby incorporated by reference for its teachings of such installation techniques and related systems, methods, and apparatuses. Other installation techniques may be used. In addition to the particular methods described here, other suitable methods exist for disposing an insulated parallel waveguide proximal to the material in which the spatial profile of moisture or related electrical properties is to be determined.

The distal end of the waveguide can terminate in an electrically shorted condition, which will cause a reversed polarity reflection of the incident voltage change. The waveguide can also terminate in an electrically open condition, in which the ends of the conductors remain electrically insulated from each other and from surrounding materials and which causes a same polarity reflection of the incident voltage change. Other termination conditions may also be used.

Step 2

To perform Step 2, electrical connection may be made from the transmission line to a TDR instrument or other measurement instrumentation, such as the TDR100 manufactured by Campbell Scientific, Inc., the HL-1101 manufactured by Hyperlabs, Inc., or the Tektronix 1503C Metallic Time Domain Reflectometer. The waveguide may be connected directly to the TDR instrument or may be connected via a length of coaxial cable or other cable between the transmission line and the TDR instrument; wireless or other types of connections may also be used. It is advantageous, but not necessary, to use a type of cable connecting the transmission line to the TDR instrument that has a characteristic impedance matching the input/output impedance of the TDR instrument, such as RG-58 A/U, RG-8, or RG-174 coaxial cable for a 50-ohm impedance, as this will maximize the transfer of incident energy into the transmission line waveguide. Other cables may also be used. The TDR instrument launches an incident pulse comprising a rapid voltage increase into the proximal end of the cable or transmission line and then measures the voltage at the point of introduction at numerous successive discrete time intervals to generate and report a discrete time series of measurements called reflectance. Reflectance ρ is a measure of the fraction of the forward traveling voltage increase reflected as backward traveling voltage by impedance changes along the transmission line. It is computed for a given reflection time t corresponding to a discrete time of voltage sample as the difference between measured voltage $V(t)$ at time t and incident voltage $V_0$ divided by the incident voltage:

$$\rho_{app}(t)=(V(t)-V_0)/V_0.$$

Figure 5:
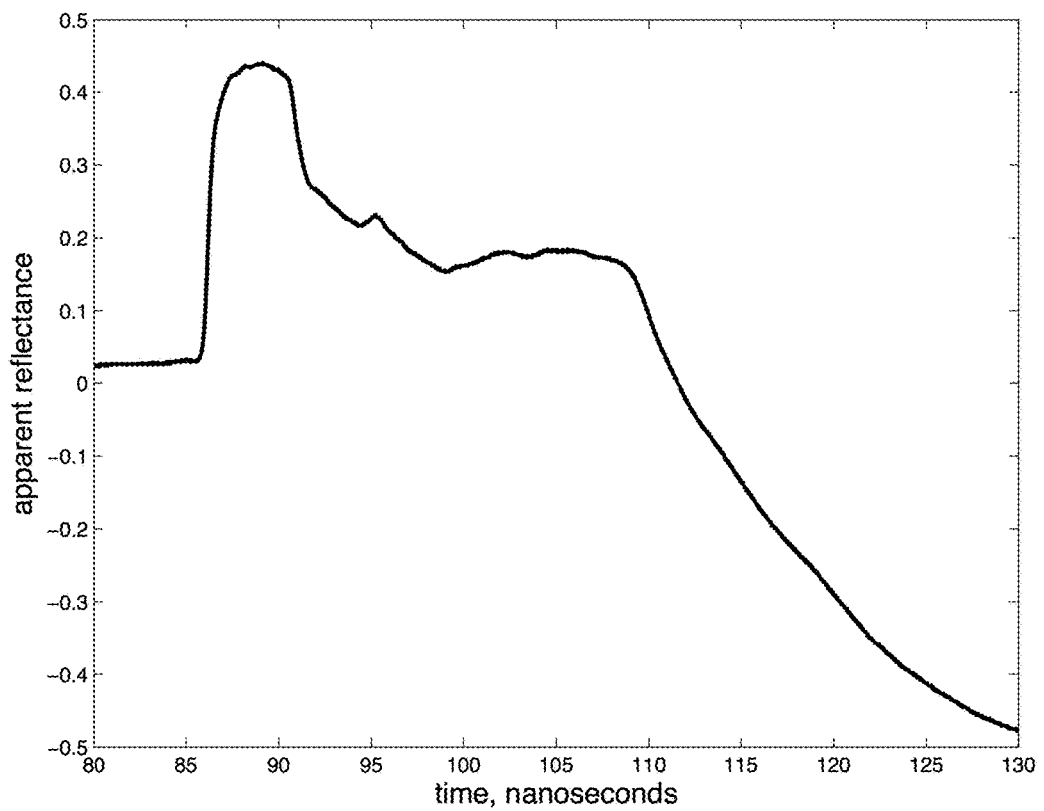
FIG. 5 is a plot of a temporal profile of apparent reflectance acquired by performing a TDR measurement of the parallel waveguide disposed proximal to a material in which the spatial profile of moisture or related electrical properties is to be determined.

A time series of hundreds or thousands of voltage or reflectance values is typically recorded by the reflectometer as a temporal profile. FIG. 5 shows a profile of apparent reflectance recorded by a reflectometer instrument.

Step 3

A particular way of converting the temporal profile of reflectance obtained in Step 2 to a temporal or spatial profile of a quantity that is indicative of electrical properties of the materials adjacent to the transmission line is to convert the temporal profile of reflectance to a temporal or spatial profile of a function of reflectance that is algebraically proportional to the dielectric of adjacent materials. One such function is:

$$f(\rho)=[(1-\rho)/(1+\rho)]^2.$$

This function has been shown to be proportional to the dielectric of materials adjacent to the transmission line by algebraic manipulation of well-known transmission line relationships. This function is particularly useful in the case when auxiliary structures adjacent to one side of the transmission line are required to dispose the transmission line proximal to the material under test in Step 1 above such that the material under test is proximal to only one side of the transmission line. In that case, it is not necessary to know the relative contributions of the media under test on one side of the waveguide and the auxiliary structures on the other side to the profile of net effective dielectric surrounding the waveguide because the dielectric of the auxiliary structures is spatially invariant and therefore the function produces a value that remains proportional to the dielectric of the media under test.

Another way of converting the temporal profile of reflectance obtained in Step 2 to a temporal or spatial profile of a quantity that is indicative of one or more electrical materials adjacent to the transmission line is to convert the temporal profile of reflectance to a temporal or spatial profile of transmission line impedance.

A particular way of converting a temporal profile of apparent reflectance $\rho_{app}$ to a profile of transmission line impedance is to apply the following relation to each value of the apparent reflectance $\rho_{app}(t)$ in the profile:

$$Z(t+\Delta t)=Z(t)[1+\rho_{app}(t)]/[1-\rho_{app}(t)],$$

in which Z(t) is the impedance just to the proximal side of a point on the transmission line corresponding to a roundtrip travel time of t, and Z(t+Δt) is the impedance just to the distal side of the point on the transmission line corresponding to a roundtrip travel time of t, being the same time the TDR instrument sampled the voltage that produced the value of apparent reflectance $\rho_{app}(t)$. Z(0) is the input/output impedance of the TDR instrument.

Another way of converting a temporal profile of apparent reflectance $\rho_{app}$ to a profile of transmission line impedance Z is to first deconvolve or dereverberate the temporal profile of apparent reflectance $\rho_{app}$ to remove multi-reflection effects also referred to as reverberation, and then to convert the profile of true reflectance $\rho_{true}$ (also called differential reflectance) to a profile of impedance Z using the following relation:

$$Z(t+\Delta t)=Z(t)[1+\rho_{true}(t)]/[1-\rho_{true}(t)].$$

One way to deconvolve the apparent reflectance profile to recover the true reflectance profile considers an idealization of the transmission line as a series of successive discrete elements, each having characteristic impedance, with changes in impedance at nodes representing junctions between elements that result in partial reflection and partial transmission of voltage changes traveling through the node from both directions.

Figure 4:
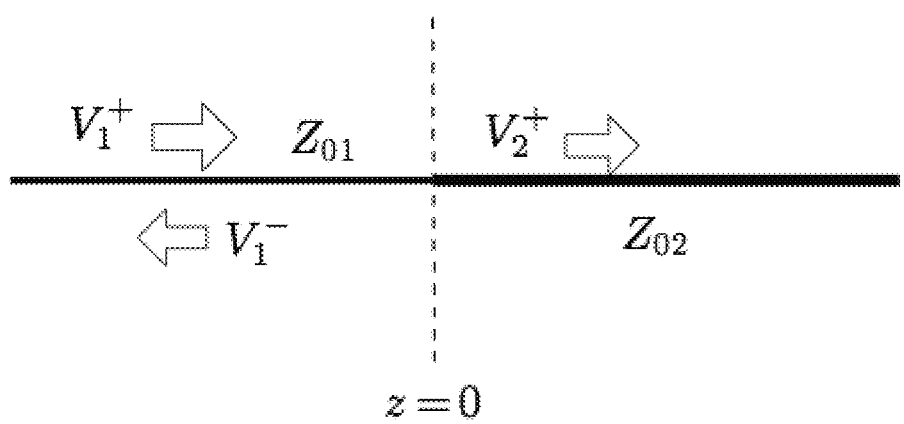
FIG. 4 is a depiction of a voltage pulse $V_1^+$ traveling from left to right encountering a change in impedance, $Z_{01}$ to $Z_{02}$, in a transmission line, resulting in partial transmission $V_2^+$ and partial reflection $V_1^-$.
Figure 14:
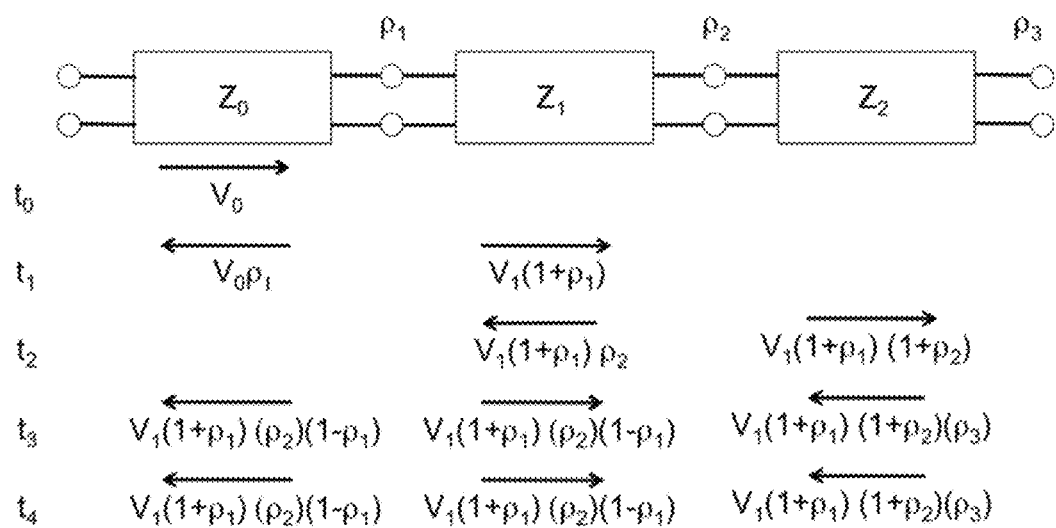
FIG. 14 is a schematic representation of a transmission line idealized as a series of infinitesimal elements each with its own impedance and equations representing the forward and backward traveling changes in voltage following introduction of an incident pulse for four time steps, each representing the travel time through an element.
Figure 15:
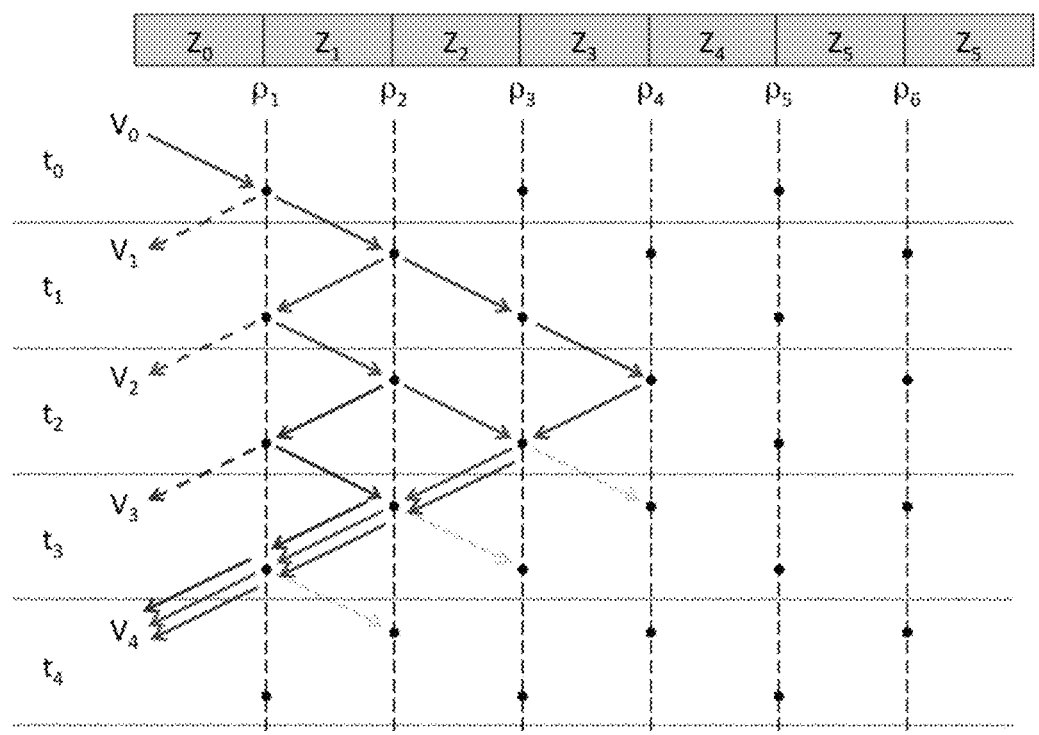
FIG. 15 is an illustration of the concept of multi-reflection on a transmission line with distance along the transmission line from left to right and time progressing from top to bottom, showing arrivals of multiple transmitted and reflected voltage changes arriving at the TDR instrument at a single time by way of several different paths.

Consider FIG. 4, which depicts a voltage pulse traveling from left to right encountering a change in impedance, $Z_{01}$ to $Z_{02}$, in a transmission line. The reflected and transmitted voltages at each change in impedance are given by the following equations:

$$V_{reflected}=\rho V_{incident}, \text{ and}$$

$$V_{transmitted}=(1-\rho)V_{incident},$$

in which the reflectance coefficient ρ is defined as:

$$\rho=(Z_{02}-Z_{01})/(Z_{02}+Z_{01}),$$

where the impedance change is from an impedance of $Z_{01}$ to an impedance of $Z_{02}$. Everywhere a change in transmission line impedance is encountered, partial reflection and partial transmission of incident voltage occur, with reflection from transitions of higher to lower impedance having polarity opposite those occurring from lower to higher impedance transitions. The voltage thus measured by the reflectometer at any instant in time can therefore be the superposed sum of multiple negative and positive polarity reflections simultaneously arriving from various multi-reflective paths resulting from impedance changes at multiple locations along the transmission line. Consider FIG. 14 which is a representation of a transmission line idealized as a series of infinitesimal elements each with its own impedance. Equations beneath each element of the transmission line represented in FIG. 14 describe the forward and backward traveling changes in voltage following introduction of an incident pulse for four time steps, each representing the travel time through an element. This phenomenon is called multi-reflection or reverberation, and is depicted as a function of time and position in FIG. 15 which depicts distance along the transmission line from left to right and time increasing from top to bottom. Diagonal arrows in FIG. 15 show arrivals of multiple transmitted and reflected voltage changes arriving at the TDR instrument by way of several different paths at each time corresponding to one of several samplings of line voltage performed by the instrument. The reflectance computed by the instrument from the net reflected voltage that includes reverberation is called the apparent reflectance, whereas the localized ratio of reflected to incident voltage that occurs at any change in impedance in a discrete infinitesimal segment of the transmission line considered in isolation is called differential reflectance or true reflectance.

This way of deconvolving the apparent reflectance profile to recover the true reflectance profile accounts for net forward and reverse traveling voltage changes on the transmission line that result from reflection and transmission of the incident voltage pulse at places of changing impedance. The time-dependent boundary condition at the instrument is known from the temporal profile of apparent reflectance. The measured net voltage V at the instrument at any point in the temporal profile can be determined from the apparent reflectance $\rho_{app}$ by multiplying the reflectance value by the magnitude of the incident voltage pulse $V_0$. The measured net voltage is the reflected voltage plus the incident voltage.

Discretization of the spatial and temporal domains treated by the deconvolution method is defined by the measurement data. Each node's location is the farthest distance from which a direct path reflection of the incident pulse could have arrived back at the instrument coincident with the corresponding sampling of voltage. The node positions, and thus length and position of each element in the discretized transmission line is not known a priori because propagation speed varies with adjacent material dielectric and the only indexing of junctions to a known spatio-temporal reference is from each junction corresponding to a discrete time sample in the temporal profile of voltage returned by the reflectometer. With the propagation velocity in each element along the round trip path of the incident voltage a variable function of the dielectric of the medium surrounding the elements, the length and thus spatial position of each element is determined once the propagation velocity between each junction has been determined using the material dielectric indicated by the element's impedance, which is recovered by dereverberating the apparent reflectance profile to yield the true reflectance profile.

The deconvolution proceeds to solve the differential reflectance at each node by considering the net voltage sensed by the TDR instrument during each time step as being composed of two parts. One part, called the single-reflected signal, is that fraction of the incident pulse attributable to a single reflection from the most distant spatial node reachable during a round-trip flight time corresponding to the sample acquisition time. The other part, also called the reverberant signal, is the portion of the sensed voltage attributable to a combination of partial reflections and transmission involving all nearer nodes over the same time interval. The contribution of single-reflected signal to the net sensed voltage is not known until it is solved for at each time step. The contribution of single-reflected signal to the net sensed voltage is determined by having already solved for the true reflectance of all closer nodes and computing the summed contributions to the sensed voltage from all but the single-reflected portion of the signal.

As this specific way of deconvolving apparent reflectance to recover a profile of true reflectance proceeds, it keeps track of the forward and backward traveling voltages arriving at each node in each time step based on the results of the previous time step. Reflections and transmissions through each node are computed, summed and numerically propagated to the next node in the corresponding direction of travel as the solution progresses through time until reflections corresponding to the distal end of the waveguide have been processed. FIG. 6 shows a true reflectance profile recovered from deconvolving an apparent reflectance profile.

Other ways of recovering the true reflectance profile from the apparent reflectance profile can also be used. Other ways of converting the temporal profile of reflectance obtained in Step 2 to a temporal or spatial profile of a quantity that is indicative of one or more electrical materials adjacent to the transmission line can be used.

Step 4

Figure 13:
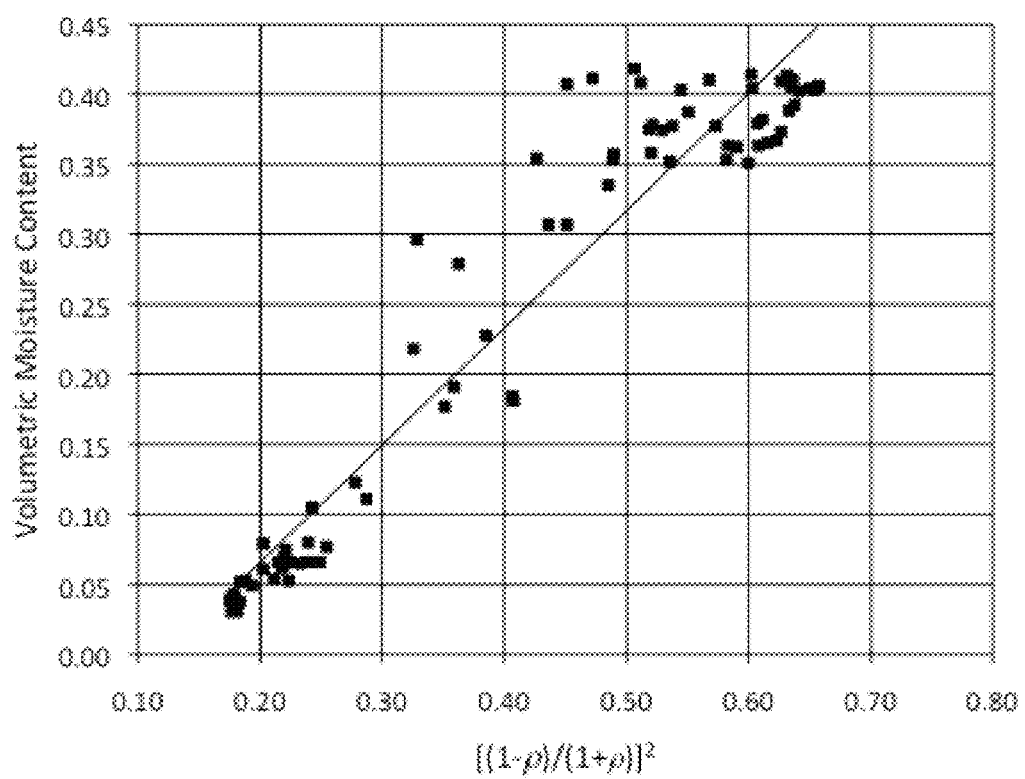
FIG. 13 is a plot showing an empirical calibration developed from experimental data relating a function of transmission line reflectance that is proportional to media dielectric to moisture content in the media.

A particular way of converting the temporal or spatial profile of a quantity that is indicative of one or more electrical properties of materials adjacent to the transmission line obtained in Step 3 to a spatial profile of moisture content, when the quantity that is indicative of the electrical properties of materials adjacent to the transmission line is the function:

$$f(\rho)=[(1-\rho)/(1+\rho)]^2,$$

which is proportional to the dielectric of the materials, is to apply an empirical calibration developed from experimental data. FIG. 13 shows one such calibration.

Another way of converting a temporal or spatial profile of a quantity that is indicative of one or more electrical properties of materials adjacent to the transmission line obtained in Step 3 to a spatial profile of moisture content, when the quantity that is indicative of the material electrical properties is the transmission line impedance, is to first convert the temporal or spatial profile of transmission line impedance to a spatial profile of material dielectric constant, also known as the relative dielectric permittivity, and then to convert the spatial profile of dielectric constant to a spatial profile of moisture content.

One particular way of converting a temporal or spatial profile of transmission line impedance to a spatial profile of material dielectric constant ε is by way of comparison of the profile of transmission line characteristic impedance to a spatial profile of the characteristic impedance of the same or identical transmission line in air, computed from a TDR measurement of the transmission line in air acquired prior to disposing the waveguide proximal to the material under test in Step 1 above, and applying a well-known formula relating the impedance of a transmission line surrounded by a material of given dielectric Z to that of the same cross sectional geometry of transmission line in air $Z_{air}$:

$$Z=Z_{air}/\varepsilon^{1/2},$$

which inverted becomes:

$$\varepsilon=(Z_{air}/Z)^2.$$

The speed of propagation of an electromagnetic wave in a transmission line is related to the dielectric permittivity and magnetic permeability of the material surrounding the conductors. The speed of propagation c in a transmission line surrounded by material is related to the speed in air by:

$$c=(\mu\varepsilon)^{-1/2},$$

in which ε is dielectric permittivity, which for air is 1, and μ is magnetic permeability, which in soils and water is negligibly different from air. Therefore the propagation speed in situ $c_{insitu}$ is related to the propagation speed in air $c_{air}$ by the material dielectric in situ $\varepsilon_{media}$ as follow:

$$c_{insitu}=c_{air}\varepsilon_{media}^{1/2}.$$

This equation can be easily seen to derive from the ratio of the speed in the transmission line surrounded by media to that in the line surrounded by air:

$$c_{insitu}/c_{air}=(\mu\varepsilon_{media})^{-1/2}/(\mu\varepsilon_{air})^{-1/2}.$$

Figure 8:
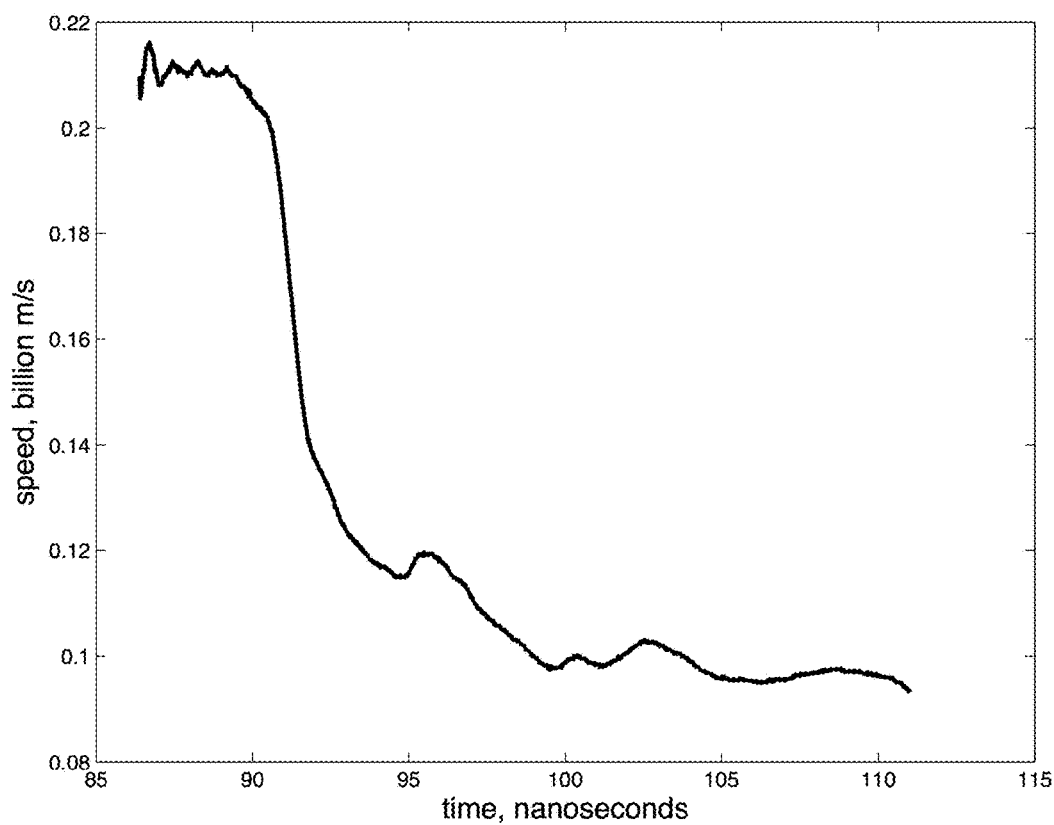
FIG. 8 is a plot showing a temporal profile of wave propagation velocity on a waveguide adjacent to media with spatially variable dielectric permittivity obtained from a temporal profile of material dielectric permittivity and the propagation velocity of the waveguide in air.
Figure 9:
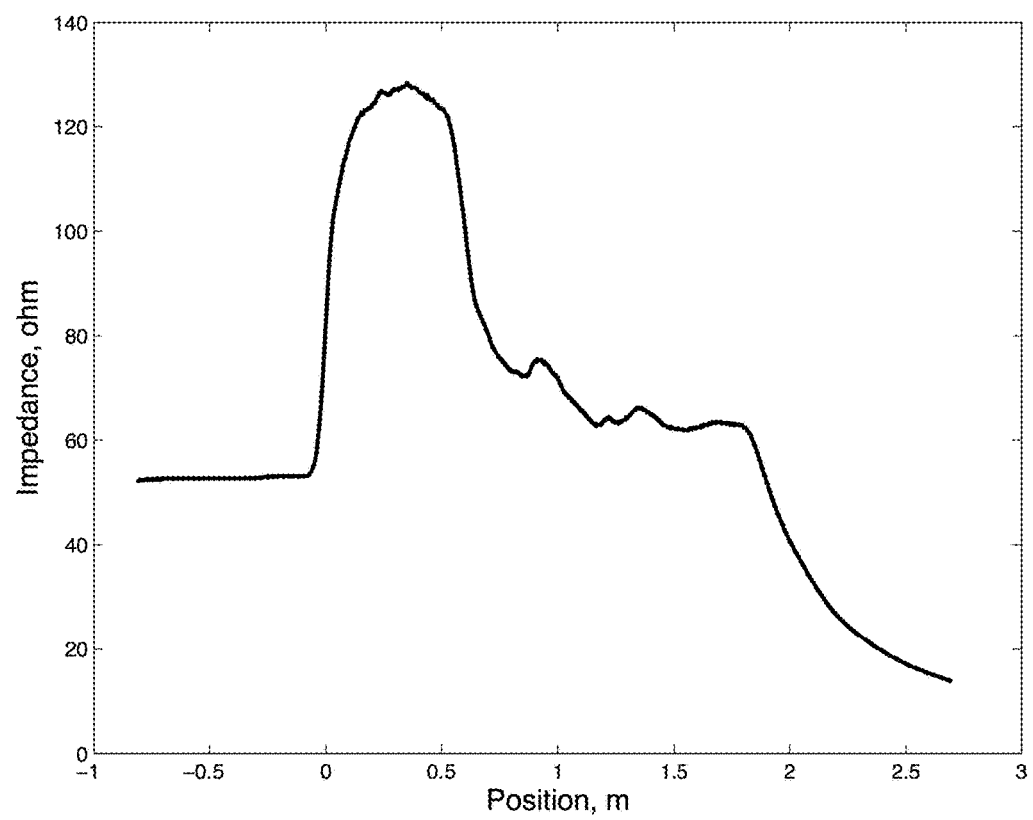
FIG. 9 is a plot showing a spatial profile of transmission line impedance obtained from a temporal profile of transmission line impedance and a temporal profile of wave propagation velocity.

FIG. 8 is a plot of a temporal profile of propagation speed on a transmission line obtained from the speed of the transmission line in air and a temporal profile of material dielectric. FIG. 9 is a plot of a spatial profile of the impedance of a transmission line surrounded by media under test obtained from the temporal profiles of the transmission line impedance and the propagation speed. The propagation speed of incident and reflected waves on the transmission line correlate more strongly to the dielectric of the surrounding media than to the media conductivity, whereas the amplitude profile of the measured signal is strongly related to both dielectric and conductivity.

In highly conductive media, losses of signal due to conductance in the media may cause the impedance profile obtained from the reflectance profile to artificially decline with increasing distance from the instrument, which causes the media dielectric profile obtained from the impedance profile to artificially increase with increasing distance from the instrument, and the profile of propagation velocity to artificially accelerate with increasing distance from the instrument. In these instances, the magnitude of the error introduced by material conductance on the amplitude of the reflectance profile and the profiles of other properties computed from the reflectance profile can be determined by comparing the position of the distal end of the waveguide, as determined from the velocity profile that was derived from the reported reflectance by way of impedance, to the known length of the waveguide. The degree of disagreement between the apparent waveguide length determined from the reflectance data and the actual length is an indication of the amount by which losses in the media affected the apparent reflectance profile reported by the instrument.

Another method of determining the amount by which losses in highly conductive media have affected the apparent reflectance profile reported by the instrument is to compare the magnitude of the final true reflection from the open circuit or short circuit terminated distal end of the transmission line to the theoretical magnitude of the final true reflection to indicate the amount by which signal losses to the media have diminished the signal reaching the distal end of the transmission line.

By examining at least one of these relationships, the relative contributions of media dielectric and media conductivity to the recovered transmission line impedance and reflectance profile can be determined, thus enabling corrections to the reflectance profile for media related losses in monotonic relation to the media dielectric constant. One particular way to adjust for media-related losses is to repeat the deconvolution step introducing a loss term into the accounting of forward and backward traveling voltages. Other ways of accounting for media related losses can also be used.

Figure 10:
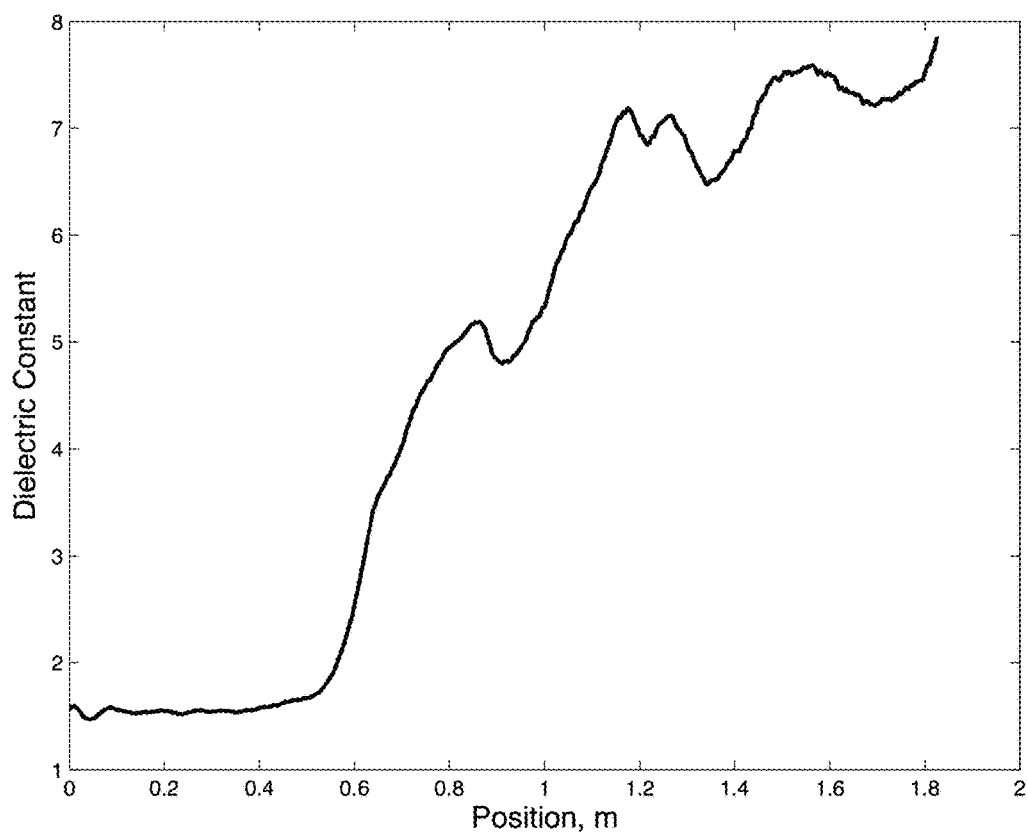
FIG. 10 is a plot showing a spatial profile of the gross effective dielectric constant of a heterogeneous mixture of materials surrounding a transmission line obtained from converting a spatial profile of transmission line impedance.

In the case that auxiliary structures adjacent to one side of the transmission line are required to dispose the transmission line proximal to the material under test in Step 1 above such that the material under test is proximal to only one side of the transmission line, then a particular way of determining the dielectric of the material under test is to first compute the gross effective dielectric of the combined auxiliary structures and material under test (see FIG. 10) by comparison to the impedance profile of the same or identical transmission line in air as described above, and to then apply an inversion of a dielectric mixing model that accounts for weighted contributions of the media under test on one side of the waveguide and the auxiliary structures on the other side to the gross effective dielectric profile.

Figure 11:
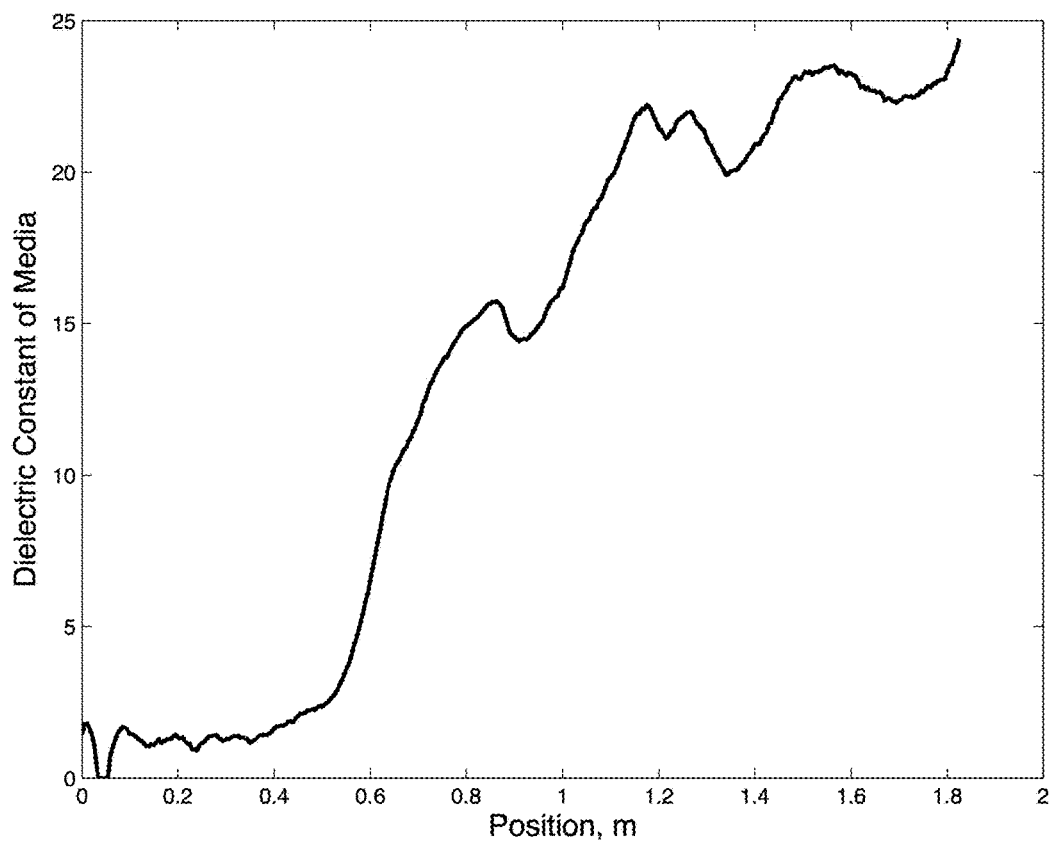
FIG. 11 is a plot showing a spatial profile of the dielectric constant of soils adjacent to one side of a transmission line obtained by application of an inverted mixing model to gross effective dielectric constant of mixed materials surrounding the transmission line.

One specific inversion of a dielectric mixing model that has been applied to find the dielectric of the media under test $\varepsilon_{media}$ is expressed as:

$$\varepsilon_{media} = \{[\varepsilon_{aux}^b(\phi-1) + \varepsilon_{eff}^b]/\phi\}^{1/b},$$

wherein $\varepsilon_{eff}$ is the gross effective dielectric of the combination of auxiliary structures and media under test determined from the in situ impedance profile, $\varepsilon_{aux}$ is the effective dielectric of the auxiliary structures experimentally determined as the square of the ratio of the impedance of the waveguide surrounded only by air to the impedance of the waveguide with adjacent auxiliary structures surrounded air, $\phi$ is the cross-sectional area fraction of the media under test relative to the combination of media and auxiliary structures, and b is an experimentally or theoretically determined exponent. For layers of media and auxiliary structures oriented in series relative to the direction of current flow, the value of b is theoretically −1, whereas for layers of media and auxiliary structures oriented in parallel relative to the direction of current flow, the value of b is theoretically +1, and for still other orientations of media and auxiliary structures relative to the direction of current flow the value of b is some other value related to the orientation. FIG. 11 is a spatial profile of soil dielectric obtained from gross effective dielectric of the soil and other structures by applying inversion of a mixing model.

Another way of converting a temporal or spatial profile of transmission line impedance to a spatial profile of a material electrical property in Step 4 is by using a previously defined relationship that relates the line impedance to the dielectric constant of a material adjacent to the line.

One particular way of establishing a relationship between line impedance and the dielectric constant of a material adjacent to the line is by numerical modeling of the transmission line impedance as a function of dielectric constant of the adjacent material over a broad range of dielectric variation. One specific method of numerically modeling the transmission line impedance as a function of dielectric constant of the adjacent material is to solve Gauss's law in a two-dimensional domain representing the cross-section of the transmission line by finite difference approximation and successive relaxation. Other methods of numerically modeling the transmission line impedance as a function of dielectric constant of the adjacent material can also be used.

In the case that auxiliary structures adjacent to one side of the transmission line are required to dispose the transmission line proximal to the material under test in Step 1 above such that the material under test is proximal to only one side of the transmission line, the numerical modeling of the transmission line impedance as a function of the dielectric properties of the adjacent materials can be performed in a manner that accounts for the influence of the auxiliary structures.

Still another way of establishing a relationship of line impedance to the dielectric constant of a material adjacent to the line is empirical determination through experimentation, in which the same transmission line prior to disposition proximal to the material under test in Step 1, or a different section of transmission line being identical in cross-section to the line in Step 1, is immersed over a portion of its length in different fluids or different mixtures of fluids having known dielectric properties and the reflectance from the point on the transmission line corresponding to the fluid interface with air is observed. Other ways of converting a temporal or spatial profile of transmission line impedance to a spatial profile of material electrical properties can also be used.

Figure 12:
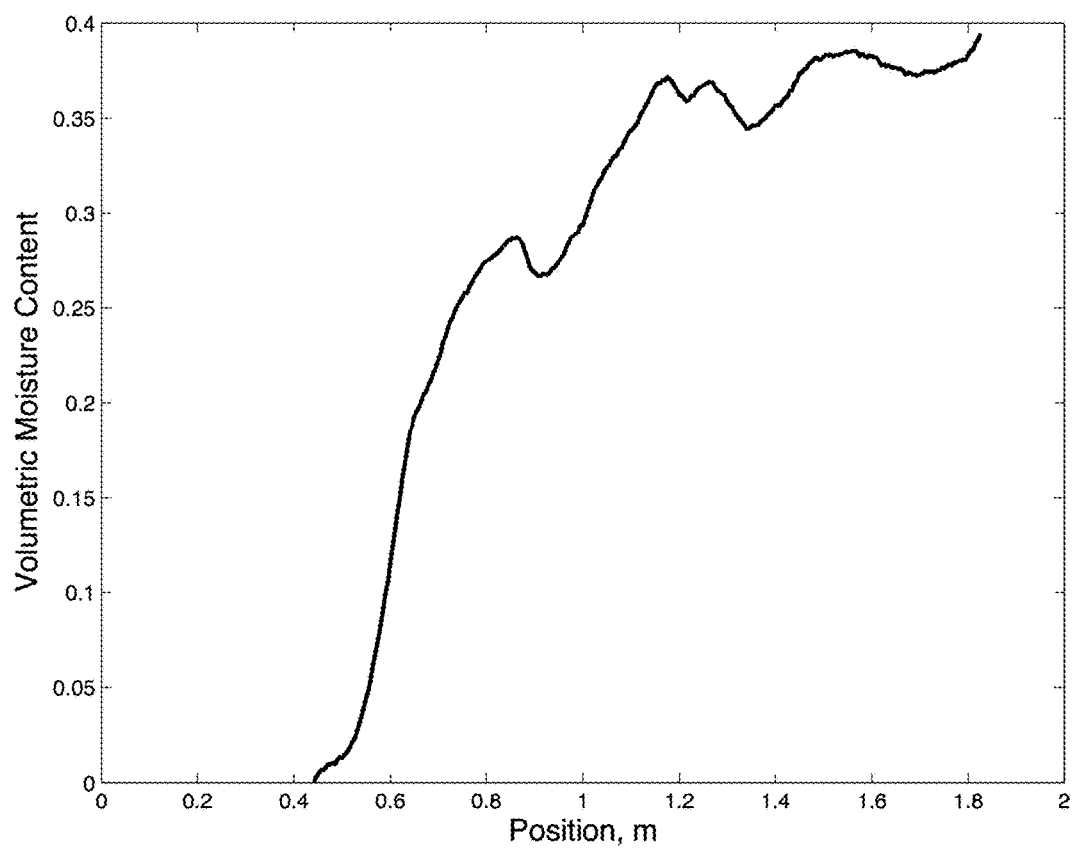
FIG. 12 is a plot showing a spatial profile of the moisture content of soils adjacent to a transmission line obtained from a spatial profile of the soil dielectric constant by application of the Topp equation.

Another particular way of converting one or more spatial profiles of material electrical properties to a spatial profile of moisture content (see FIG. 12) in Step 4 pertains to a soil material when the spatial profile of a material electrical properties is a profile of dielectric constant, also known as the relative dielectric permittivity, is to apply well-known equations relating volumetric water content to soil dielectric, such as the Topp Equation, Volumetric Water Content=$-5.3 \times 10^{-2} + 2.92 \times 10^{-2} \varepsilon^{1/2} - 5.5 \times 10^{-4} \varepsilon^2 + 4.3 \times 10^{-6} \varepsilon^3$ and the Ledieu equation, Volumetric Water Content=$0.1138\varepsilon^{1/2} - 0.1758.$ Another way of converting a spatial profile of material dielectric constant to a spatial profile of soil moisture content is to apply a soil-specific empirical calibration developed from experimental data. Other ways of converting one or more spatial profiles of material electrical properties to a spatial profile of moisture content when the spatial profile of material electrical properties is a profile of dielectric constant can also be used. Other ways of converting one or more spatial profiles of material electrical properties to a spatial profile of moisture content when the spatial profile of material electrical properties is not a profile of dielectric constant can also be used. Other ways of converting the temporal or spatial profile a quantity that is indicative of one or more electrical properties of materials adjacent to the transmission line obtained in Step 3 to a spatial profile of moisture content can also be used.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 22:
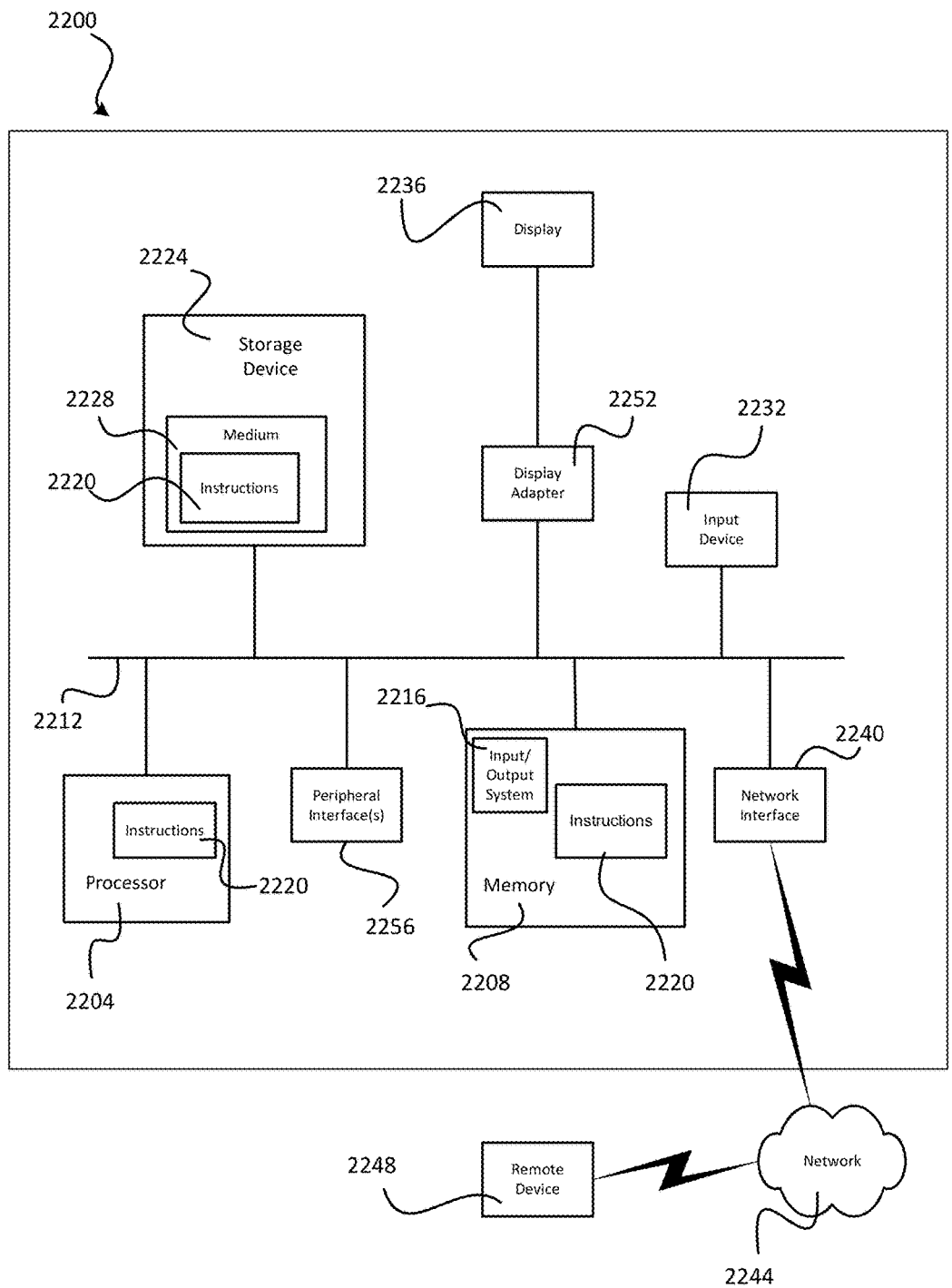
FIG. 22 is a block diagram of a computing system that can be used to implement any one or more of the methodologies disclosed herein and any one or more portions thereof.

FIG. 22 shows a diagrammatic representation of one embodiment of a computing device in the exemplary form of a computer system 2200 within which a set of instructions for causing a control system, such as the measurement instrumentation 7 of FIG. 1 and/or other control systems, to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 2200 includes a processor 2204 and a memory 2208 that communicate with each other, and with other components, via a bus 2212. Bus 2212 may include any of several types of bus structures including, but not limited to, a memory bus, a memory controller, a peripheral bus, a local bus, and any combinations thereof, using any of a variety of bus architectures.

Memory 2208 may include various components (e.g., machine-readable media) including, but not limited to, a random access memory component, a read only component, and any combinations thereof. In one example, a basic input/output system 2216 (BIOS), including basic routines that help to transfer information between elements within computer system 2200, such as during start-up, may be stored in memory 2208. Memory 2208 may also include (e.g., stored on one or more machine-readable media) instructions (e.g., software) 2220 embodying any one or more of the aspects and/or methodologies of the present disclosure. In another example, memory 2208 may further include any number of program modules including, but not limited to, an operating system, one or more application programs, other program modules, program data, and any combinations thereof.

Computer system 2200 may also include a storage device 2224. Examples of a storage device (e.g., storage device 2224) include, but are not limited to, a hard disk drive, a magnetic disk drive, an optical disc drive in combination with an optical medium, a solid-state memory device, and any combinations thereof. Storage device 2224 may be connected to bus 2212 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 2224 (or one or more components thereof) may be removably interfaced with computer system 2200 (e.g., via an external port connector (not shown)). Particularly, storage device 2224 and an associated machine-readable medium 2228 may provide nonvolatile and/or volatile storage of machine-readable instructions, data structures, program modules, and/or other data for computer system 2200. In one example, software 2220 may reside, completely or partially, within machine-readable medium 2228. In another example, software 2220 may reside, completely or partially, within processor 2204.

Computer system 2200 may also include an input device 2232. In one example, a user of computer system 2200 may enter commands and/or other information into computer system 2200 via input device 2232. Examples of an input device 2232 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 2232 may be interfaced to bus 2212 via any of a variety of interfaces (not shown) including, but not limited to, a serial interface, a parallel interface, a game port, a USB interface, a FIREWIRE interface, a direct interface to bus 2212, and any combinations thereof. Input device 2232 may include a touch screen interface that may be a part of or separate from display 2236, discussed further below. Input device 2232 may be utilized as a user selection device for selecting one or more graphical representations in a graphical interface as described above.

A user may also input commands and/or other information to computer system 2200 via storage device 2224 (e.g., a removable disk drive, a flash drive, etc.) and/or network interface device 2240. A network interface device, such as network interface device 2240, may be utilized for connecting computer system 2200 to one or more of a variety of networks, such as network 2244, and one or more remote devices 2248 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 2244, may employ a wired and/or a wireless mode of communication. In general, any network topology may be used. Information (e.g., data, software 2220, etc.) may be communicated to and/or from computer system 2200 via network interface device 2240.

Computer system 2200 may further include a video display adapter 2252 for communicating a displayable image to a display device, such as display device 2236. Examples of a display device include, but are not limited to, a liquid crystal display (LCD), a cathode ray tube (CRT), a plasma display, a light emitting diode (LED) display, and any combinations thereof. Display adapter 2252 and display device 2236 may be utilized in combination with processor 2204 to provide graphical representations of aspects of the present disclosure. In addition to a display device, computer system 2200 may include one or more other peripheral output devices including, but not limited to, an audio speaker, a printer, and any combinations thereof. Such peripheral output devices may be connected to bus 2212 via a peripheral interface 2256. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A method of determining spatially variable distributions of one or more electrical properties of a material having at least one dielectric constant, the method comprising:

disposing an insulated parallel waveguide proximal to the material;

using the insulated parallel waveguide to perform a time domain reflectometry (TDR) measurement to acquire a first temporal profile of apparent reflectance of the waveguide;

converting the first temporal profile of apparent reflectance of the waveguide to a second temporal profile of a quantity that is indicative of the one or more electrical properties of a portion of the material adjacent to the waveguide;

converting the second temporal profile to a spatial profile of moisture content of the material by correlating impedance characteristics associated with the waveguide to the one or more electrical properties of the portion of the material adjacent to the waveguide as a function of a predetermined relationship; and making the spatial profile of moisture content available to a user for analysis or other use.

2. A method according to claim 1, wherein the waveguide is disposed in or on a probe, the probe comprising a non-metallic tube, rod, or other rigid structure.

3. A method according to claim 1, wherein the waveguide terminates in an electrically shorted condition.

4. A method according to claim 1, wherein the waveguide terminates in an electrically open condition.

5. A method according to claim 1, wherein the making the spatial profile of moisture content available to a user for analysis or other use includes at least one of displaying the spatial profile of moisture content on a display, storing the spatial profile of moisture content on a computer readable medium, or transmitting the spatial profile of moisture content to another device.

6. A method according to claim 1, wherein the second temporal profile is a profile of true reflectance, further wherein the first temporal profile of apparent reflectance is based on a net voltage measurement sensed by a TDR instrument at a measurement location, the net voltage measurement including a single-reflected portion based on a voltage reflection from a first location in the insulated parallel waveguide and a reverberant portion based on voltage reflections and transmissions from locations within the insulated parallel waveguide between the measurement location and the first location, wherein said converting the first temporal profile to the temporal profile of true reflectance includes deconvolving or dereverberating the net voltage measurement to remove the reverberant portion of the net voltage measurement.

7. A method according to claim 6, wherein said deconvolving or dereverberating includes tracking the voltage reflections and transmissions at a plurality of locations within the insulated parallel waveguide.

8. A method according to claim 7, wherein said tracking includes computing a first reflection from and first transmission through a location in the insulated parallel waveguide, and using the first computed transmission to compute a second reflection from and a second transmission through an adjacent location in the insulated parallel waveguide.

9. A method according to claim 1, wherein the second temporal profile is a profile of true reflectance, further wherein said converting the second temporal profile further includes converting the profile of true reflectance to a profile of impedance.

10. A method according to claim 1, wherein the predetermined relationship is determined via numerically modeling one or more characteristic impedances of the insulated parallel waveguide as a function of one or more dielectric constants of materials disposed adjacent to the waveguide.

11. A method according to claim 1, wherein the predetermined relationship is determined via performing a plurality of TDR measurements of a second insulated parallel waveguide when the second insulated parallel waveguide is disposed proximal to a plurality of different media each having one or more known electrical properties, wherein the second insulated parallel waveguide is the same or substantially the same as the insulated parallel waveguide.

12. A non-transitory machine-readable storage medium containing machine-executable instructions for performing a method of determining spatially variable distributions of one or more electrical properties of a material having at least one dielectric constant, said machine-readable instructions comprising:

a first set of machine-executable instructions for using an insulated parallel waveguide disposed proximal to the material to perform a time domain reflectometry measurement to acquire a first temporal profile of apparent reflectance of the waveguide;

a second set of machine-executable instructions for converting the first temporal profile of apparent reflectance of the waveguide to a second temporal profile of a quantity that is indicative of the one or more electrical properties of a portion of the material adjacent to the waveguide;

a third set of machine-executable instructions for converting the second temporal profile to a spatial profile of moisture content of the material by correlating impedance characteristics associated with the waveguide to the one or more electrical properties of the portion of the material adjacent to the waveguide as a function of a predetermined relationship; and a fourth set of machine-executable instructions for making the spatial profile of moisture content available to a user for analysis or other use.

* * * * *